US008137625B2

(12) United States Patent
Sasanuma et al.

(10) Patent No.: US 8,137,625 B2
(45) Date of Patent: Mar. 20, 2012

(54) UREA SENSOR

(75) Inventors: Takeo Sasanuma, Komaki (JP);
Yoshikuni Sato, Komaki (JP); Akihiro Yoshida, Komaki (JP)

(73) Assignee: NGK Spark Plug Co., Ltd., Nagoya (JP)

( * ) Notice: Subject to any disclaimer, the term of this patent is extended or adjusted under 35 U.S.C. 154(b) by 1043 days.

(21) Appl. No.: 12/016,580

(22) Filed: Jan. 18, 2008

(65) Prior Publication Data
US 2008/0205478 A1 Aug. 28, 2008

(30) Foreign Application Priority Data

Jan. 22, 2007 (JP) .............................. P2007-011838
Dec. 17, 2007 (JP) .............................. P2007-324895

(51) Int. Cl.
*G01N 33/00* (2006.01)

(52) U.S. Cl. .................... 422/82.02; 422/68.1; 436/108; 436/149; 436/150

(58) Field of Classification Search .................. None
See application file for complete search history.

(56) References Cited

U.S. PATENT DOCUMENTS

| 7,469,574 | B2 | 12/2008 | Kawanishi et al. | |
|---|---|---|---|---|
| 7,574,900 | B2 * | 8/2009 | Sasanuma et al. | ........... 73/61.46 |
| 7,712,363 | B2 * | 5/2010 | Sasanuma et al. | .............. 73/295 |
| 7,829,024 | B2 | 11/2010 | Izutani et al. | |
| 2007/0054409 | A1 | 3/2007 | Inoue et al. | |
| 2008/0066531 | A1 | 3/2008 | Kawanishi et al. | |
| 2008/0247912 | A1 | 10/2008 | Izutani et al. | |
| 2009/0090178 | A1 | 4/2009 | Sasanuma et al. | |

FOREIGN PATENT DOCUMENTS

| EP | 1669742 A1 | 6/2006 |
|---|---|---|
| EP | 1906176 A1 | 4/2008 |
| JP | 2005-084025 A | 3/2005 |
| JP | 2005-337969 A | 12/2005 |
| JP | 2007010587 A | 1/2007 |
| WO | 2007004583 A1 | 1/2007 |

OTHER PUBLICATIONS

European Patent Office, Extended European Search Report (EESR) for counterpart European Application No. 08001121.6, mailed Dec. 14, 2010.
JPO, Office Action issued in corresponding application JP 2007-324895, dispatched Nov. 22, 2011.

* cited by examiner

*Primary Examiner* — Jill Warden
*Assistant Examiner* — Monique Cole
(74) *Attorney, Agent, or Firm* — Stites & Harbison PLLC; Jeffrey A. Haeberlin

(57) ABSTRACT

A urea sensor includes a detecting portion which, in use, is immersed in a liquid accommodated in a urea solution tank for detecting the thermal conductivity of the liquid to detect whether the liquid accommodated in the urea solution tank is an aqueous urea solution; and an enclosing member enclosing a periphery of the detecting portion and including one or more vents penetrating the enclosing member. At least one of the vents is a lower vent being of a configuration and size such that a first hypothetical circle having a diameter of not less than 3.5 mm can be wholly contained within the lower vent. At least a portion of the lower vent is positioned below the detecting portion when the urea sensor is positioned for installation in the urea solution tank.

19 Claims, 12 Drawing Sheets

UREA SENSOR

FIELD OF THE INVENTION

The present invention relates to a urea sensor.

BACKGROUND OF THE INVENTION

An NOx selective reduction catalyst (SCR) is in some cases used in an exhaust gas purifying apparatus for reducing nitrogen oxides (NOx) emitted from, for example, a diesel powered automobile, and an aqueous urea solution is used as its reductant. It is known that an aqueous urea solution with a urea concentration of 32.5 wt % can be advantageously used for effectively performing this reducing reaction. However, in the aqueous urea solution accommodated in a urea solution tank mounted in a diesel powered automobile, there are cases where the urea concentration changes due to such as a change over time. In addition, there is also a possibility of a different type of solution (such as light oil) or water becoming erroneously mixed into the urea solution tank. In view of such circumstances, urea sensors (urea concentration identifying devices) have been proposed to manage the urea concentration of the aqueous urea solution in the urea solution tank (e.g., refer to JP-A-2005-84026 (corresponding to US2007/00544091A1)).

The urea concentration identifying device in JP-A-2005-84026 (corresponding to US2007/00544091A1) is designed to provide an identifying device for a urea solution which is capable of accurately and speedily identifying the urea concentration of the urea solution even during the traveling of a vehicle. Namely, a concentration identifying sensor portion is provided with an indirectly heated concentration detecting portion and a liquid temperature detecting portion (detecting portion) each having a metallic fin. Further, this concentration identifying sensor portion (liquid concentration detecting element) is provided with a cover member for forming a urea solution introducing passage in such a way as to surround the metallic fins, as well as an enclosure with circulation holes respectively formed in upper and lower end face plates thereof.

SUMMARY OF THE INVENTION

The reason for providing such a configuration is as follows. In general, a urea solution which properly reflects the states, such as the concentration and the temperature, of the entire urea solution stored in a tank or the like needs to be located around the detecting portions (the indirectly heated concentration detecting portion and the liquid temperature detecting portion) of the concentration detecting element (concentration identifying sensor portion). For this reason, the circulation of the liquid needs to be provided around these detecting portions in order to allow the urea solution to be able to appropriately undergo liquid exchange with the urea solution outside the urea sensor (urea concentration identifying device). Meanwhile, in a case where the urea solution around the detecting portions moves violently, it becomes difficult to appropriately detect the states of the urea solution such as the concentration and the temperature owing to that effect, so that an error in the measurement value of concentration can possibly become large.

Incidentally, there is a possibility that a driver or an operator erroneously pours light oil into the urea solution tank by mistaking the urea solution tank for a light oil tank. It should be noted that since the light oil has a smaller specific gravity than the aqueous urea solution, in the event that the light oil has been mixed in the urea solution tank, the aqueous urea solution is located on a vertically downward side, while the light oil is located on a vertically upward side. In this case, in the state in which the aqueous urea solution has decreased due to use and the liquid level has dropped below the urea sensor, if the liquids (aqueous urea solution and light oil) in the urea solution tank violently move due to the effect of vibrations and the like, there have been cases where droplets of the aqueous urea solution enter the interior of the enclosing member (enclosure).

However, according to an investigation made by the present inventors, there have been cases where even if vents are provided in a lower portion of the enclosing member for the purpose of liquid circulation, the aqueous urea solution which entered the interior of the enclosing member cannot be appropriately discharged to outside the enclosing member, and the aqueous urea solution accumulates only inside the enclosing member even if the light oil is located outside (around the periphery of) the enclosing member, thereby setting the detecting portions in a state of being surrounded by the aqueous urea solution. In that case, despite the abnormal situation in which the liquid level of the aqueous urea solution has dropped below the detecting portions and the light oil which has been erroneously added into the urea solution tank might be supplied to the catalyst, there has been a possibility that the urea sensor erroneously detects that the appropriate aqueous urea solution is being accommodated in the urea solution tank. In addition, also in a case where a liquid fuel, such as gasoline, having a smaller specific gravity than the aqueous urea solution has been erroneously poured into the urea solution tank, there has been a possibility of occurrence of a problem similar to that of the case where light oil has been added, as described above.

The present invention has been devised in view of the above-described circumstances, and its object is to provide a urea sensor which makes it possible to prevent the erroneous detection that an appropriate aqueous urea solution is contained in the urea solution tank in the case where a liquid fuel, such as light oil, having a smaller specific gravity than the aqueous urea solution has been mistakenly added to the urea solution tank and the liquid level of the aqueous urea solution has dropped below the urea sensor.

To attain the above object, in accordance with a first aspect of the invention there is provided a urea sensor comprising: a detecting portion, which, in use, is immersed in a liquid accommodated in a urea solution tank, for detecting the thermal conductivity of the liquid so as to detect whether the liquid accommodated in the urea solution tank is an aqueous urea solution; and an enclosing member enclosing a periphery of the detecting portion and including one or more vents penetrating the enclosing member; wherein at least one of the one or more vent comprises a lower vent being of a configuration and size such that a hypothetical circle having a diameter of not less than 3.5 mm can be wholly contained within the lower vent, said lower vent being disposed such that at least a portion of the lower vent is located closer to a downwardly extending end of the urea sensor than the detecting portion when the urea sensor is positioned for installation in the urea solution tank.

In the urea sensor in accordance with the above-described first aspect of the invention, at least one of the vents of the enclosing member is formed as a lower vent in which a first hypothetical circle with a diameter of not less than 3.5 mm can be included. As a result, even if droplets of the aqueous urea solution have entered the interior of the enclosing member in a state in which a liquid fuel (a different type of liquid), such as light oil, having a smaller specific gravity than the aqueous urea solution has been mistakenly added to the urea solution tank, the aqueous urea solution can be discharged to outside the enclosing member through the lower vent. Hence, the liquid fuel, such as light oil, having a smaller specific gravity than the aqueous urea solution can fill the enclosure around the detecting portion as around the outer portion (periphery) of the enclosing member.

In the urea sensor in accordance with the invention, it is possible to prevent the erroneous detection that the appropriate aqueous urea solution is contained in the urea solution tank in the case where a liquid fuel, such as light oil, having a smaller specific gravity than the aqueous urea solution has been mistakenly added to the urea solution tank and the liquid level of the aqueous urea solution has dropped below the detecting portion. Namely, in the case where a liquid fuel (which also applies to a different type of liquid having a different thermal conductivity than the aqueous urea solution), such as light oil, having a smaller specific gravity than the aqueous urea solution has been mistakenly added to the urea solution tank, it is possible to appropriately detect that a different type of liquid having a different thermal conductivity than the aqueous urea solution is present.

It should be noted that since this type of urea sensor is frequently used by being installed in a urea solution tank which is mounted in a diesel powered automobile, there is a high risk of light oil, in particular, being mistakenly added to the urea solution tank by mistaking the urea solution tank for a light oil tank. However, in the urea sensor in accordance with the invention, since it is possible to appropriately detect that a different type of liquid (light oil) is present in the urea solution tank, it is possible to prevent the defect that, for instance, the light oil which has been erroneously poured into the urea solution tank is unfavorably supplied to the catalyst.

In addition, it is possible for the form of the lower vent to be, for example, a circular vent with a diameter of not less than 3.5 mm, an elliptical vent with a short diameter of not less than 3.5 mm, a vent in which a plurality of slits each having a width of not less than 3.5 mm intersect each other, or a vent consisting of a circular vent with a diameter of not less than 3.5 mm and slits extending radially from this vent. It should be noted that the lower vent is sufficient if it has such a form as to allow a first hypothetical circle with a diameter of not less than 3.5 mm to be disposed, or wholly contained, within the lower vent. As such, however, the lower vent should preferably discharge aqueous urea solution to the outside of the enclosing member when the urea solution tank is in a stationary state (i.e., the urea sensor is in a stationary state), even if droplets of the aqueous urea solution have entered the interior of the enclosing member, when a liquid fuel, such as light oil, having a smaller specific gravity than the aqueous urea solution has been mistakenly added to the urea solution tank. From this viewpoint, the first hypothetical circle should preferably have a diameter of not less than 5.0 mm.

In accordance with a second aspect of the invention, there is provided a urea sensor comprising: a detecting portion which, in use, is immersed in a liquid accommodated in a urea solution tank, for detecting the thermal conductivity of the liquid so as to detect whether the liquid accommodated in the urea solution tank is an aqueous urea solution; and an enclosing member enclosing a periphery of the detecting portion and including a plurality of vents penetrating the enclosing member;

wherein the plurality of vents include a lower vent located closer to a vertically downwardly extending end of the urea sensor than the detecting portion when the urea sensor is positioned for installation in the urea solution tank, and an upper vent located closer to a vertically upwardly extending end of the urea sensor than a lower end of the detecting portion; and wherein a maximum diameter of a first hypothetical circle which can be wholly contained within the lower vent is greater than a maximum diameter of a second hypothetical circle which can be wholly contained within the upper vent.

In the urea sensor in accordance with the above-described second aspect of the invention, as the plurality of vents provided in the enclosing member, there are provided a lower vent located closer to the vertically downwardly extending end than the detecting portion and an upper vent located closer to a vertically upwardly extending end than a lower end of the detecting portion, and the size of the lower vent is set to a size which satisfies a specific relationship with the upper vent. Specifically, the respective vents are set so as to satisfy the relationship that a maximum diameter of a first hypothetical circle which can be disposed in the lower vent is greater than a maximum diameter of a second hypothetical circle which can be disposed in the upper vent.

When the urea sensor is positioned for installation, the upper vent mainly functions to introduce droplets of the aqueous urea solution into the enclosing member, but as the size of the lower vent relative to this upper vent is set to a size which satisfies the above-described specific relationship, even if droplets of the aqueous urea solution have entered the interior of the enclosing member in a state in which a liquid fuel, such as light oil, having a smaller specific gravity than the aqueous urea solution has been mistakenly added to the urea solution tank, the aqueous urea solution can be discharged to outside the enclosing member through the lower vent.

Accordingly, in the urea sensor in accordance with the invention, it is possible to prevent problems of erroneously detecting that the appropriate aqueous urea solution is present in the urea solution tank in the case where a liquid fuel, such as light oil, having a smaller specific gravity than the aqueous urea solution has been mistakenly added to the urea solution tank and the liquid level of the aqueous urea solution has dropped below the detecting portion.

It should be noted that, in accordance with a third aspect of the invention, the maximum diameter of the first hypothetical circle may be not more than two-fold, or twice, the maximum diameter of the second hypothetical circle. If the size of the maximum diameter of the first hypothetical circle is made excessively large relative to the maximum diameter of the second hypothetical circle, even in a case where vibrations (e.g., vibrations occurring during the operation of a diesel powered automobile) have been applied to the aqueous urea solution accommodated in the urea solution tank and a liquid flow directed upward from the vertically downward side has occurred, the effect of the liquid flow can be exerted on the detecting portion through the lower vent, possibly causing a decline in the detection accuracy of the detecting portion. Accordingly, the effect of the liquid flow is made difficult to be exerted on the detecting portion as the maximum diameter of the first hypothetical circle which is included in the lower vent is set to not more than two-fold by using as a reference the maximum diameter of the second hypothetical circle which mainly functions to introduce droplets of the aqueous urea solution and is included in the upper vent.

In addition, in the urea sensor in accordance with a fourth aspect of the invention, the maximum diameter of the first hypothetical circle may be not less than 3.5 mm.

By setting the maximum diameter of the first hypothetical circle to not less than 3.5 mm, even if droplets of the aqueous urea solution have entered the interior of the enclosing member in a state in which a liquid fuel, such as light oil, having a smaller specific gravity than the aqueous urea solution is erroneously accommodated in the urea solution tank, the aqueous urea solution can be satisfactorily discharged to outside the enclosing member through the lower vent.

It should be noted that the lower vent is sufficient if it has such a form as to allow the first hypothetical circle with a diameter of not less than 3.5 mm to be disposed in the lower vent. As such, however, the lower vent should preferably such that when the urea solution tank is in a stationary state (i.e., the urea sensor is in a stationary state), even if droplets of the aqueous urea solution have entered the interior of the enclosing member in a state in which a liquid fuel, such as light oil, having a smaller specific gravity than the aqueous urea solution has been mistakenly added to the urea solution tank, the aqueous urea solution can be discharged to outside the enclosing member through the lower vent. From this viewpoint, the first hypothetical circle should preferably have a diameter of not less than 5.0 mm.

Furthermore, in the urea sensor in accordance with a fifth aspect of the invention, the lower vent of the enclosing member may be set in a form in which the first hypothetical circle faces the vertically downward side when the urea sensor is positioned for installation.

In the urea sensor in accordance with the invention, the lower vent of the enclosing member is set in a form in which the first hypothetical circle faces the vertically downward side of the urea sensor as positioned for installation in the urea solution tank. As a result, the aqueous urea solution which entered the interior of the enclosing member, as described above, can be easily discharged to outside the enclosing member, so that this arrangement is favorable.

Furthermore, in the urea sensor in accordance with a sixth aspect of the invention, the enclosing member may have a bottomed cylindrical shape (i.e., a circular bottom wall and a cylindrical side wall extending upward from the bottom wall) having a bottom wall facing the downwardly extending end of the urea sensor as positioned for installation, and the lower vent may be disposed in the bottom wall.

In the urea sensor in accordance with the invention, the enclosing member has a bottom wall facing the vertically downward side, and the lower vent is disposed in the bottom wall. As a result, even in a case where vibrations (e.g., vibrations occurring during the operation of a diesel powered automobile) have been applied to the aqueous urea solution accommodated in the urea solution tank and a liquid flow directed upward from the downward end has occurred, the aqueous urea solution can be discharged to the outside through the lower vent while alleviating that liquid flow from affecting the detecting portion at the bottom portion of the enclosing member.

Furthermore, in accordance with a seventh aspect of the invention, the urea sensor may further comprise a flow controlling member which has a flow controlling surface provided on the vertically downward side of the first hypothetical circle of the lower vent and opposing the first hypothetical circle when the urea sensor is positioned for installation, wherein the flow controlling surface is set in a form in which when the flow controlling surface is projected toward the first hypothetical circle on the vertically upward side, the first hypothetical circle in its entirety is included in a projected region of the flow controlling opposing surface, and wherein a distance between the flow controlling opposing surface and the first hypothetical circle is not less than 3.0 mm.

In the aqueous urea solution accommodated in the urea solution tank, a liquid flow directed upward from the vertically downward side can occur due to the effect of vibrations (e.g., vibrations occurring during the operation of a diesel powered automobile). Meanwhile, in a case where the enclosing member is provided with the lower vent in which the first hypothetical circle faces the vertically downward side, as described above, such a liquid flow enters the interior of the enclosing member through the lower vent without weakening of the momentum of the liquid flow. The aqueous urea solution around the detecting portion can move violently due to this effect, with the result that there is a possibility that it becomes impossible to appropriately perform the detection as to whether the liquid accommodated in the urea solution tank is the aqueous urea solution or a different type of liquid having a different thermal conductivity therefrom.

In contrast, in the urea sensor in accordance with the invention, a flow controlling member having a flow controlling surface opposing the first hypothetical circle is provided on the vertically downward side of the lower vent. This flow controlling surface is set in a form in which when the flow controlling surface is projected toward the first hypothetical circle on the vertically upward side, the first hypothetical circle in its entirety is included in the projected region of the flow controlling opposing surface. In other words, when the urea sensor in accordance with the invention is positioned for installation in the urea solution tank, and the vertically upward side is viewed from the vertically lower side of the urea sensor, the first hypothetical circle included in the lower vent is shielded by that portion of the flow controlling member which constitutes the flow controlling opposing surface.

Accordingly, even if a liquid flow directed from the vertically lower side toward the vertically upper side of the urea sensor has occurred in the urea solution tank, it is possible to prevent this liquid flow from entering the enclosing member directly through the lower vent by virtue of the presence of that portion of the flow controlling member which constitutes the flow controlling surface. As a result, it is possible to appropriately suppress the effect exerted by such a liquid flow on the detection of whether the liquid accommodated in the urea solution tank is the aqueous urea solution or a different type of liquid having a different thermal conductivity therefrom.

Moreover, in the urea sensor in accordance with the invention, a distance of not less than 3.0 mm is provided between the flow controlling surface and the lower vent. By so doing, the discharge of droplets of the aqueous urea solution, which entered the interior of the enclosing member as described above, to outside the enclosing member through the lower vent is not hampered by the flow controlling member (flow controlling opposing surface). Namely, droplets of the aqueous urea solution, which entered the interior of the enclosing member as described above, can be appropriately discharged to outside the enclosing member through the lower vent.

Furthermore, in the urea sensor in accordance with an eighth aspect of the invention, the detecting portion may have a temperature rise portion in which a heating resistor whose resistance value changes in correspondence with a temperature thereof is liquid-tightly sealed in a ceramic insulating substrate.

In the case where a different type of liquid having a different thermal conductivity from the aqueous urea solution is erroneously accommodated in the urea solution tank, if this different type of solution is heated by the heating resistor, the rate of temperature rise differs from the case where the aqueous urea solution is accommodated due to the difference in the thermal conductivity. For example, a different type of liquid, such as light oil, having a smaller thermal conductivity from the aqueous urea solution has a smaller rate of temperature rise as compared to the aqueous urea solution.

The urea sensor in accordance with the invention has a temperature rise portion whose heating resistor is liquid-tightly sealed in a ceramic insulating substrate. For this reason, if the temperature rise portion having the heating resistor is immersed in the liquid accommodated in the urea solution tank and the heating resistor is energized, the rate of temperature rise of that liquid (i.e., the liquid type) exerts an effect on the temperature rise of the heating resistor. Since this heating resistor has a resistance value corresponding to its own temperature, a difference arises in the resistance value of the heating resistor after a predetermined time period of energization owing to the difference in the thermal conductivity of the liquid (difference in the liquid type) accommodated in the urea solution tank. Accordingly, it becomes possible to appropriately detect whether the liquid accommodated in the urea solution tank is the aqueous urea solution or a different type of liquid (such as light oil) having a different thermal conductivity therefrom on the basis of an output value outputted in correspondence with the resistance value of the heating resistor.

Incidentally, the urea concentration identifying device of JP-A-2005-84026 (corresponding to US2007/00544091A1) has an indirectly heated concentration detecting portion having an element in which a substrate, a temperature sensing element, an insulating layer, a heating element, and a protective layer are sequentially stacked. In this urea concentration identifying device, the heating element is energized for a predetermined time period, and the urea concentration is detected on the basis of a temperature change of the heating element measured by the temperature sensing element before and after the energization.

In contrast, in the urea sensor in accordance with the invention, since the heating resistor having a resistance value corresponding to its own temperature is used, as described above, it is possible to detect whether the liquid accommodated in the urea solution tank is the aqueous urea solution or a different type of liquid having a different thermal conductivity therefrom on the basis of an output value outputted in correspondence with the resistance value of the heating resistor. Accordingly, unlike the urea concentration identifying device of JP-A-2005-84026 (corresponding to US2007/00544091A1), it is unnecessary to provide a temperature sensing element for sensing the temperature of the heating resistor. For this reason, as compared with the urea concentration identifying device of JP-A-2005-84026 (corresponding to US2007/00544091A1), the urea sensor in accordance with the invention makes it possible to simplify the configuration of the detecting portion and make it compact, so that this arrangement preferable.

Furthermore, in the urea sensor in accordance with a ninth aspect of the invention, the temperature rise portion may have a temperature-rise-portion main surface having a largest heat-generating area and a temperature-rise-portion reverse surface located on an opposite side thereto, wherein in a case where the urea sensor is provided with the flow controlling member, the enclosing member may be formed such that each of the vents excluding at least the lower vent is disposed at a position which frontally or directly faces neither the temperature-rise-portion main surface nor the temperature-rise-portion reverse surface, whereas in a case where the urea sensor is not provided with the flow controlling member, the enclosing member may be formed such that each of the vents including the lower vent is disposed at a position which frontally faces neither the temperature-rise-portion main surface nor the temperature-rise-portion reverse surface.

In the aqueous urea solution accommodated in the urea solution tank, a liquid flow can occur due to the effect of vibrations (e.g., vibrations occurring during the operation of a diesel powered automobile). Meanwhile, vents are formed in the enclosing member surrounding the periphery of the detecting portion. For this reason, in a case where a liquid flow has occurred in the urea solution tank, the liquid flow can enter the interior of the enclosing member through the vents without weakening of the momentum of the liquid flow. At this time, in the case where the vents in the enclosing member are disposed at positions where they frontally face the temperature rise main surface and the temperature rise reverse surface, the aqueous urea solution adjacent to the temperature rise main surface and the temperature rise reverse surface can move violently. Hence, there is a possibility that it becomes impossible to appropriately perform the detection as to whether the liquid accommodated in the urea solution tank is the aqueous urea solution or a different type of liquid having a different thermal conductivity therefrom.

In contrast, in the urea sensor in accordance with the invention, in the case where the urea sensor is provided with the flow controlling member, the enclosing member is formed such that each of the vents excluding at least the lower vent is disposed at a position which frontally or directly faces neither the temperature-rise-portion main surface nor the temperature-rise-portion reverse surface. Alternatively, in the case where the urea sensor is not provided with the flow controlling member, the enclosing member is formed such that each of the vents including the lower vent is disposed at a position which frontally or directly faces neither the temperature-rise-portion main surface nor the temperature-rise-portion reverse surface. As a result, even if the liquid flow has entered the interior of the enclosing member through the vents, this liquid flow does not directly strike the temperature-rise-portion main surface and the temperature-rise-portion reverse surface, and it is possible to prevent the aqueous urea solution adjacent to the temperature-rise-portion main surface and the temperature-rise-portion reverse surface from moving violently. Therefore, in the urea sensor in accordance with the invention, even if a liquid flow has occurred inside the urea solution tank, it is possible to appropriately perform in the detecting portion the detection of whether the liquid accommodated in the urea solution tank is the aqueous urea solution or a different type of liquid having a different thermal conductivity therefrom.

Other features and advantages of the invention will be set forth in, or apparent from, the detailed description of preferred embodiments of the invention found below.

DETAILED DESCRIPTION OF EXEMPLARY EMBODIMENTS OF THE INVENTION

Hereafter, a description will be given of exemplary embodiments of a urea sensor in accordance with the invention. A urea sensor 1 in accordance with one embodiment shown in FIG. 1 is used as a device for detecting the urea concentration of an aqueous urea solution LQ1 or a liquid level LQH of the aqueous urea solution LQ1 accommodated in a urea solution tank 10 in an exhaust gas purifying apparatus for reducing and rendering harmless nitrogen oxides ($NO_x$) contained in exhaust gases of an automotive vehicle with, for example, a diesel engine mounted thereon, by the aqueous urea solution LQ1.

Figure 1:
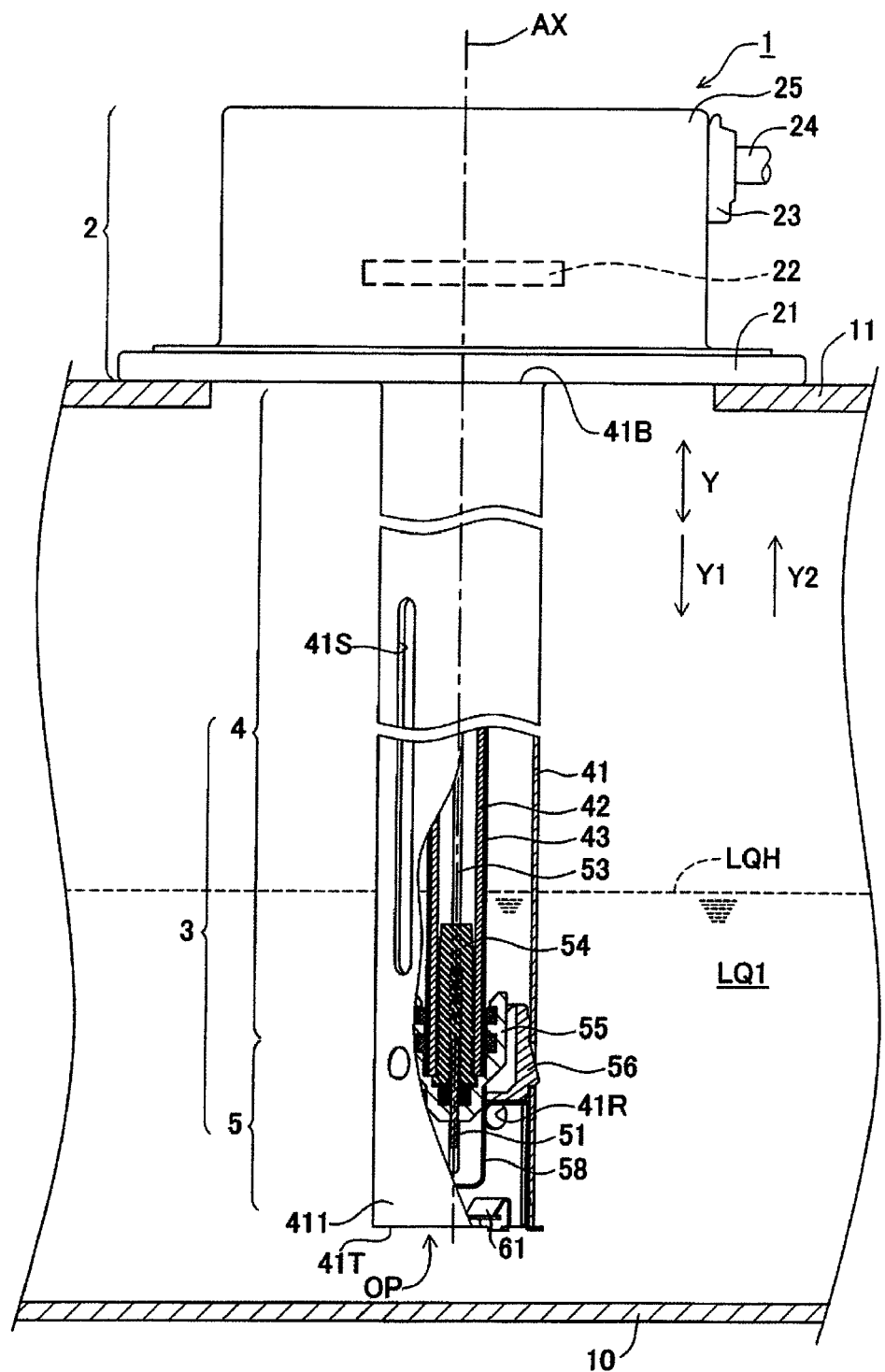
FIG. 1 is a front elevational view with selected portions cut-away of a urea sensor immersed in a urea solution tank, in accordance with an exemplary embodiment of the invention.

This urea sensor 1 (hereafter, also referred to as the sensor 1) is comprised of a base portion 2 and a sensor portion 3 extending downward in FIG. 1 from this base portion 2. This urea sensor 1 is used by mounting the base portion 2 around an opening of the urea solution tank 11 in which the aqueous urea solution LQ1 indicated by the broken line is accommodated, by positioning the sensor portion 3 in such an attitude as to extend in a vertical direction Y (up-down direction in FIG. 1), and by immersing the sensor portion 3 in the aqueous urea solution LQ1.

It should be noted that, in this specification, unless otherwise specified, a description will be given of this sensor 1 and its respective parts in the attitude in which the sensor 1 is installed in the urea solution tank 10 (in the attitude shown in FIG. 1). Accordingly, when the sensor 1 is set in the attitude (i.e., "positioned for installation") in which it is installed in the urea solution tank 10, as shown in FIG. 1, the direction (axial direction) along an axis AX of the sensor 1 is the vertical direction Y (up-down direction in FIG. 1). The vertically downward direction along the axis AX is denoted Y1, while the vertically upward direction is denoted Y2.

In the urea sensor 1, the base portion 2 includes a mounting flange 21, a cover 25, a wiring board 22 enclosed by them, an external connection cable 24, and a bushing 23 for holding it. In addition, the sensor portion 3 consists of a double cylindrical liquid level sensor portion 4 and a urea concentration sensor portion 5. It should be noted that, in the attitude in which the urea sensor 1 is installed (i.e., the installation position) in the urea solution tank 10, as shown in FIG. 1, the urea concentration sensor portion 5 is arranged to be located closer to the vertically downward side Y1 than the liquid level sensor portion 4.

First, a description will be given of the base portion 2. The mounting flange 21 is formed of a metal and is used as a seat for mounting the urea sensor 1 to the opening 11 of the urea solution tank 10. Unillustrated bolt insertion holes are formed in this mounting flange 21, so that the urea sensor 1 (base portion 2) is so arranged as be fixed to the urea solution tank 10 with bolts.

Meanwhile, the wiring board 22 indicated by the broken line in FIG. 1 is disposed closer to the vertically upward side Y2 than this mounting flange 21. A control circuit (not shown) having a CPU, electric circuits, and the like is formed on this wiring board 22. This control circuit is electrically connected to the liquid level sensor portion 4 and the urea concentration sensor portion 5, and is connectable to an external electric circuit through the external connection cable 24. In addition, this wiring board 22 is covered by the cover 25 fitted to the mounting flange 21 so as to be liquid-tightly protected.

Through the energization of a concentration sensor element 51 (shown in FIG. 3A) of the urea concentration sensor portion 5, the control circuit formed on this wiring board 22 detects the urea concentration of the aqueous urea solution LQ1 on the basis of an output signal corresponding to a resistance value of an internal heater wiring 518, specifically on the basis of a potential difference (voltage value) occurring across both ends of the internal heater wiring 518 as a predetermined current is allowed to flow across the concentration sensor element 51.

Next, a description will be given of the sensor portion 3. As described above, this sensor portion 3 consists of the liquid level sensor portion 4 and the urea concentration sensor portion 5. Of these, the liquid level sensor portion 4 will be described first, and the urea concentration sensor portion 5 will be described later.

As shown in FIG. 1, the liquid level sensor portion 4 includes an outer cylinder 41 of a hollow cylindrical shape extending in the vertical direction Y (up-down direction in FIG. 1), as well as an inner cylinder 42 of a hollow cylindrical shape which is disposed in its interior, is concentric with this outer cylinder 41, but has a relatively smaller diameter. The inner peripheral surface of the outer cylinder 41 and the outer peripheral surface of the inner cylinder 42 are spaced apart from each other with a predetermined interval therebetween.

Of these, the outer cylinder 41 is formed of a metal and serves as one electrode for detecting the liquid level LQH. Additionally, the outer cylinder 41 has a narrow elongated elliptical slit 41S whose longitudinal direction is the vertical direction Y (up-down direction in FIG. 1), such that the outer cylinder 41 in a state of communication with the outside is capable of accommodating the aqueous urea solution LQ1 in the space between it and the inner cylinder 42. In addition, a lower end 41T of the outer cylinder 41 is open to form a lower end opening OP, while an upper end 41B thereof is secured to the mounting flange 21 by welding or the like.

Figure 2:
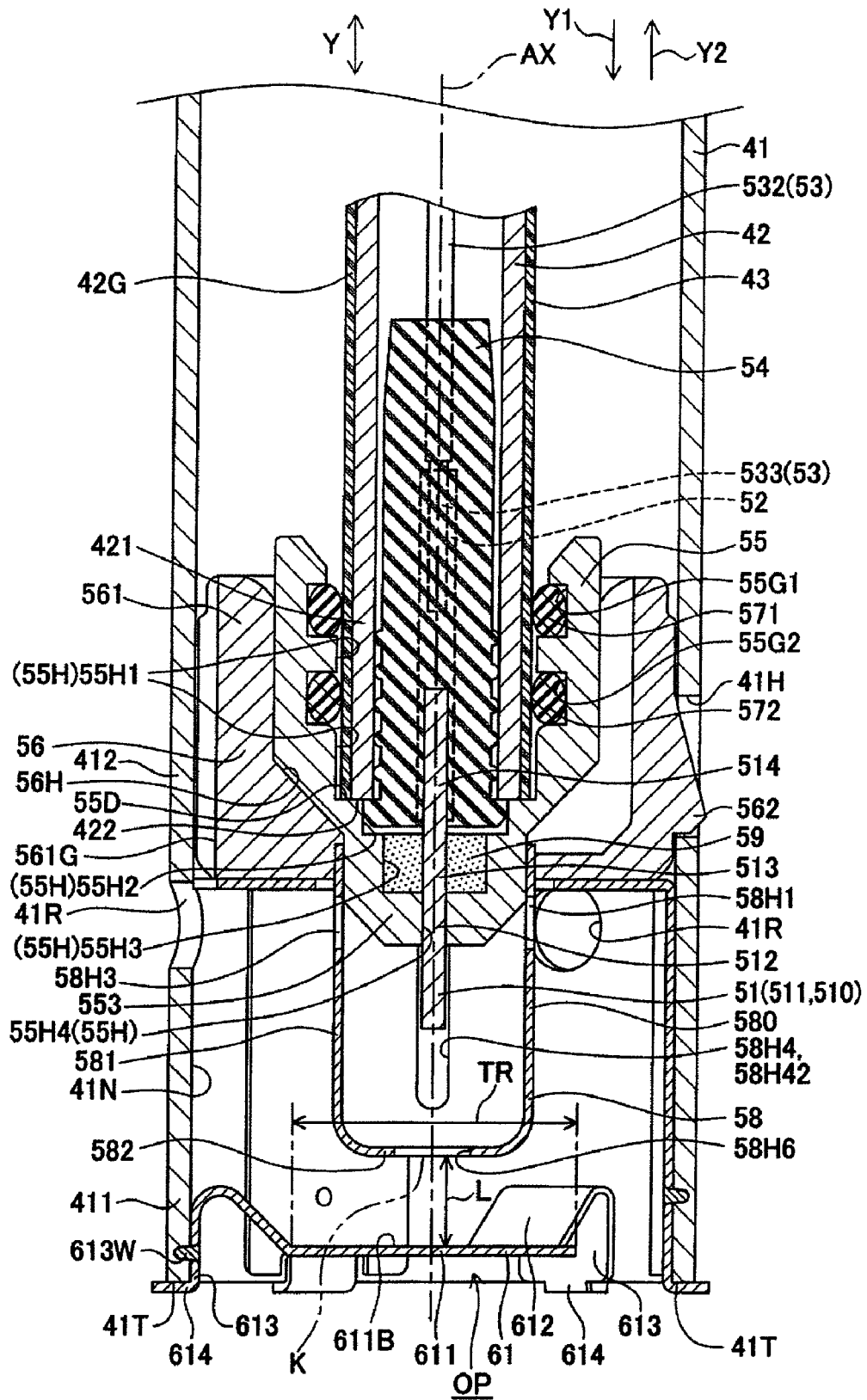
FIG. 2 is a longitudinal cross-sectional view of a urea concentration sensor portion of the urea sensor of FIG. 1.

It should be noted that in the sensor 1 of this embodiment the outer cylinder 41 is welded to the mounting flange 21. Further, this mounting flange 21 is connected to the ground potential in the control circuit (not shown) formed on the wiring board 22, thereby setting the outer cylinder 41 at the ground potential. In addition, as shown in FIG. 2 in enlarged form, a rubber bushing 56, which will be described later, is interposed between a holding portion 412 located slightly upwardly of the lower end 41T of the outer cylinder 41 and a lower end portion 421 of the inner cylinder 42 located on the downward side. Holding holes 41H for holding this rubber bushing 56 (urea concentration sensor portion 5) by respectively engaging retaining projecting portions 562 formed on the outer periphery of this rubber bushing 56 are formed in the holding portion 412 of the outer cylinder 41 at a plurality of predetermined circumferential positions (3 positions in this embodiment). Further, circulation holes 41R for ensuring circulation of the aqueous urea solution LQ1 with the interior of the outer cylinder 41 are bored on the side below the holding holes 41H.

In addition, the inner cylinder 42 is also formed of a metal and serves as the other electrode for measuring the liquid level LQH. The inner cylinder 42 is electrically connected to the control circuit on the wiring board 22 in such a manner as to oppose the outer cylinder 41 while being electrically insulated from the outer cylinder 41. An outer peripheral surface 42G of the inner cylinder 42 is clad with an insulating film 43 formed of a fluorocarbon resin such as PTFE, PFA, and ETFE, an epoxy resin, a polyimide resin, or the like, so that the inner cylinder 42 is electrically insulated from the outer cylinder 41 even in the presence of the aqueous urea solution LQ1 between the inner cylinder 42 and the outer cylinder 41.

To detect the liquid level LQH of the aqueous urea solution LQ1 by this liquid level sensor portion 4, this liquid level sensor portion 4 is immersed in the aqueous urea solution LQ1, and the aqueous urea solution LQ1 is allowed to flow into the space between the outer cylinder 41 and the inner cylinder 42 (insulating film 43) through the slit 41S.

Then, in this liquid level sensor portion 4, a portion where the aqueous urea solution LQ1 is present and a portion where it is absent are formed between the outer cylinder 41 and the inner cylinder 42 in correspondence with the liquid level LQH, so that the electrostatic capacity of a capacitor formed between the outer cylinder 41 and the inner cylinder 42 changes in correspondence with the liquid level LQH. Accordingly, if an ac voltage is applied across the outer cylinder 41 and the inner cylinder 42, an electric current corresponding to the magnitude of this electrostatic capacity flows, so that the liquid level LQH of the aqueous urea solution LQ1 can be detected by ascertaining the magnitude of the electric current.

Next, a description will be given of the urea concentration sensor portion 5.

As shown in FIG. 1 through FIG. 3B, the urea concentration sensor portion 5 is disposed on the vertically downward side Y1 of the liquid level sensor portion 4, and is comprised of the concentration sensor element 51, a holder member 55, an enclosing member 58, the rubber bushing 56.

Of these, the concentration sensor element 51 is held in the holder member 55 in a form in which its lower end portion protrudes therefrom. In addition, the concentration sensor element 51 is electrically connected to the control circuit formed on the wiring board 22 through a pair of connection terminals 52 and a pair of connection cables 53 (see FIGS. 2 and 3A) which are secured thereto by soldering. Meanwhile, the holder member 55 is held in the holding portion 412 of the outer cylinder 41 by the rubber bushing 56 interposed between the holder member 55 and the outer cylinder 41 surrounding it. Further, the enclosing member 58 is held by engaging a lower end portion (small-diameter portion 553) of the holder member 55 in such a manner as to enclose a lower end portion 511 of the concentration sensor element 51 which protrudes from the holder member 55.

First, a description will be given of the concentration sensor element 51 (see FIG. 3A) of the urea concentration sensor portion 5. This concentration sensor element 51 has a rectangular flat shape in a plan view and has two flat ceramic layers 519 (519A, 519B) formed of an alumina ceramic and an internal wiring 516 which is liquid-tightly disposed therebetween. This internal wiring 516 includes a pair of wide internal lead wirings 517 as well as the internal heater wiring 518 disposed therebetween and arranged in a serpentine pattern or folded up and down in the form of a bellow.

Figure 3A:
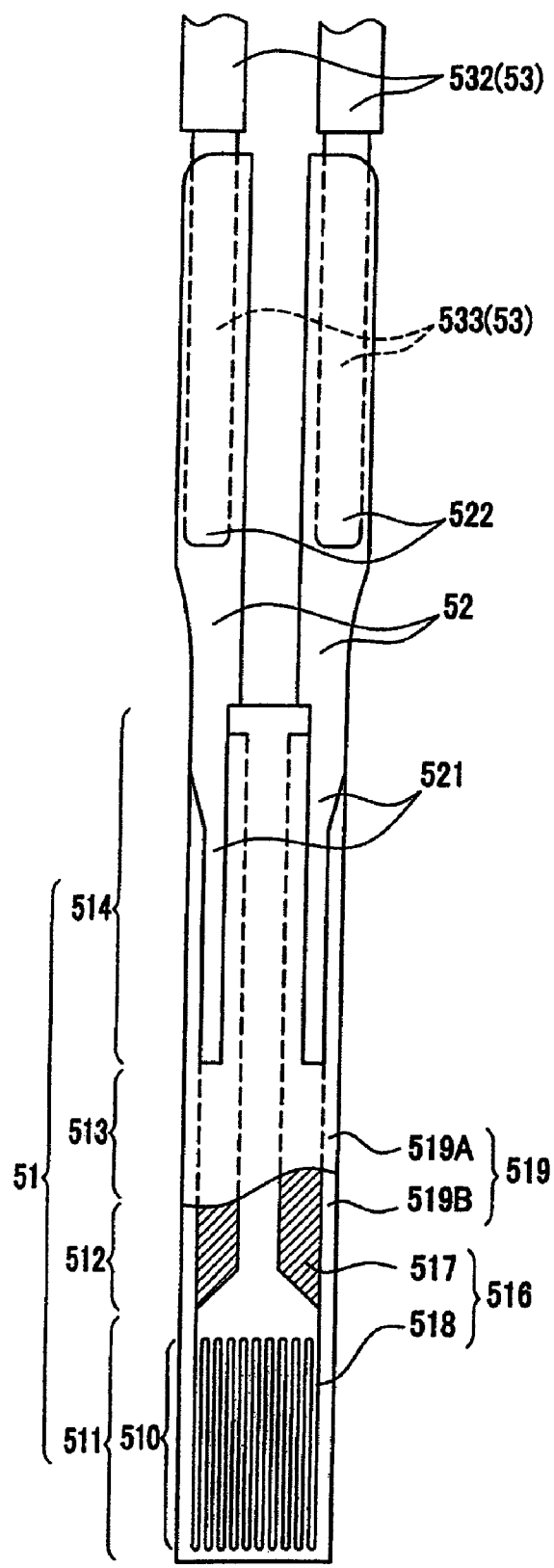
FIG. 3A is a front elevational view with selected portions cut-away of a concentration sensor element of the urea sensor of FIG. 1, showing respective connections, connection terminals, and lead wires.

In addition, as shown in FIGS. 2 and 3A, this concentration sensor element 51 is comprised of the lower end portion 511 protruding from the holder member 55; an insertion portion 512 which is adjacent to the vertically upward side Y2 of this lower end portion 511 and is inserted in the holder member 55; a resin holding portion 513 located on the vertically upward side Y2 of this insertion portion 512; and an upper end portion 514 to which the pair of connection terminals 52 are respectively connected by soldering.

Figure 3B:
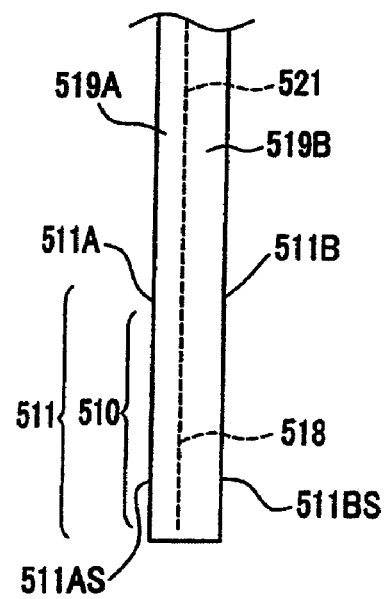
FIG. 3B is a side elevational view of a leading end portion of the concentration sensor element of FIG. 3A.
Figure 4:
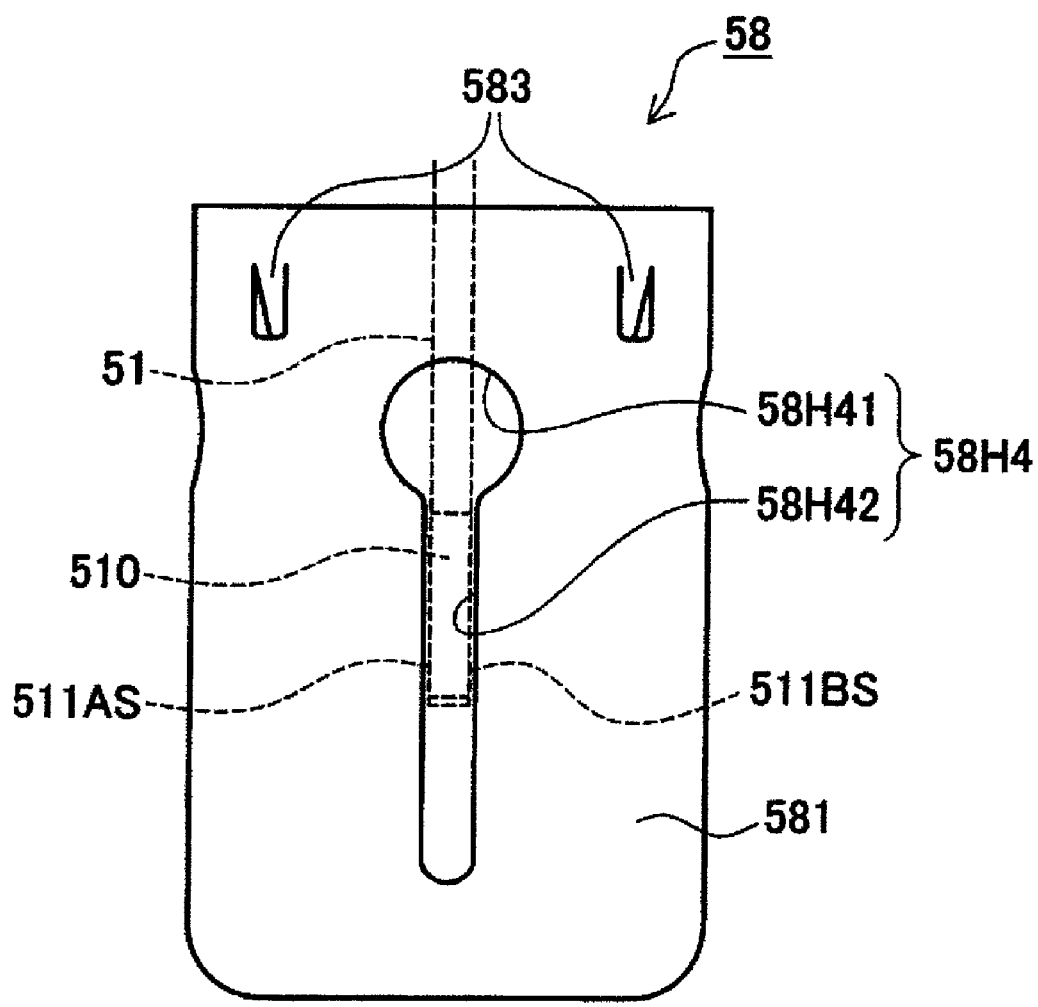
FIG. 4 is a front elevational view of an enclosing member of the urea sensor of FIG. 1.
Figure 5:
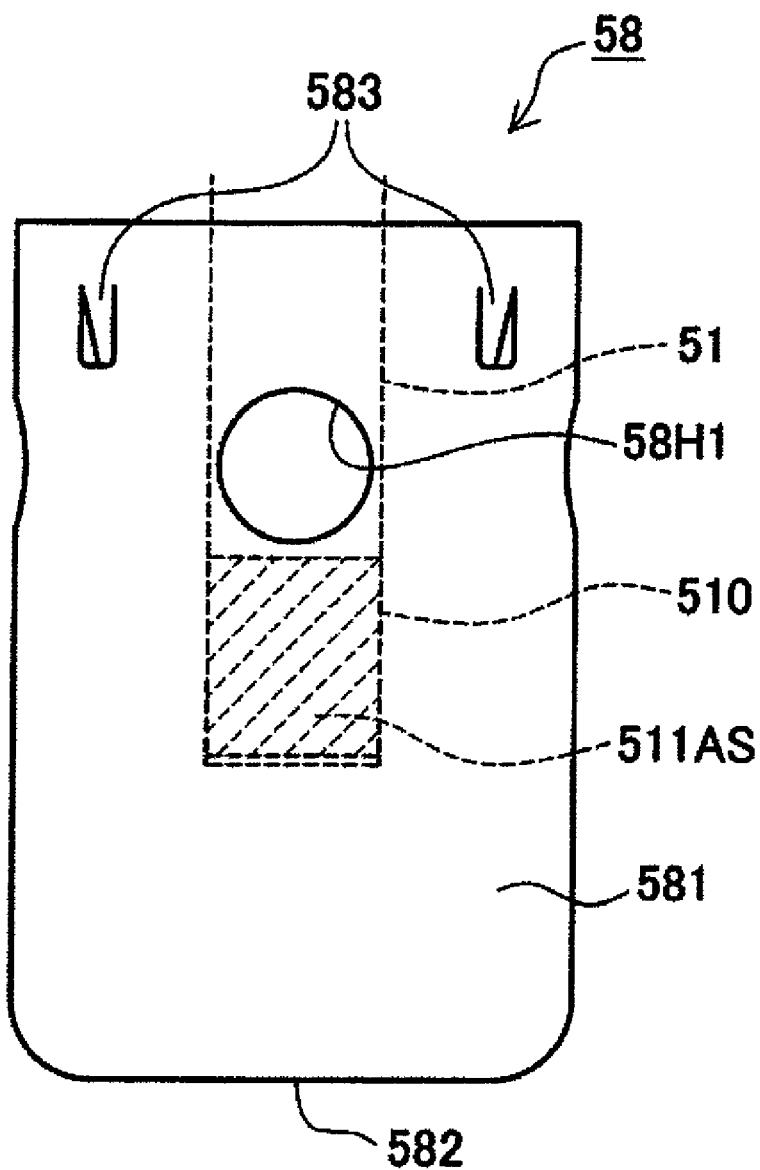
FIG. 5 is a left side elevational view of the enclosing member of FIG. 4.
Figure 6:
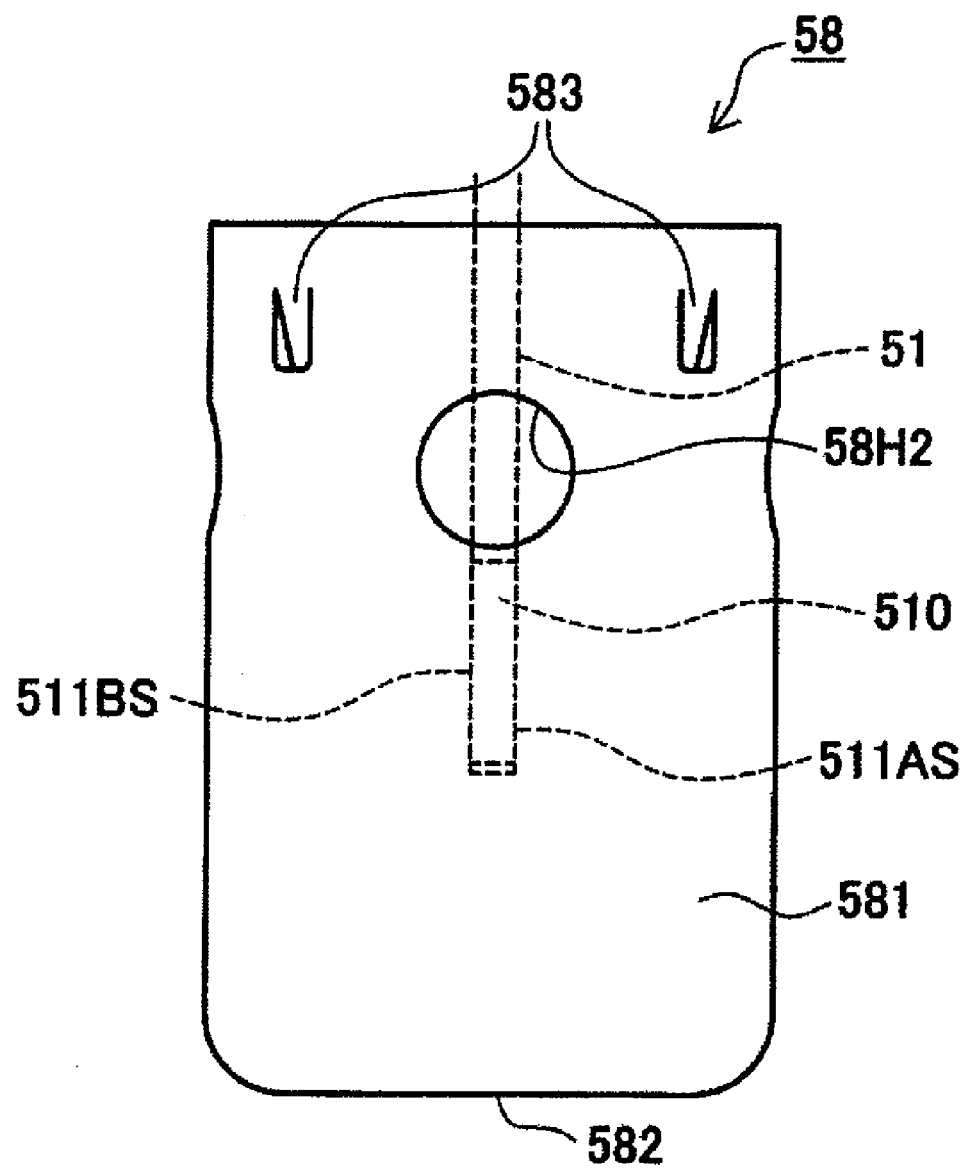
FIG. 6 is a rear elevational view of the enclosing member of FIG. 4.

As shown in FIG. 3A, the internal heater wiring 518 is disposed in the lower end portion 511. Accordingly, in this embodiment, a temperature rise detecting portion 510 having a flat plate shape is included in the lower end portion 511. The temperature rise detecting portion 510 undergoes a temperature rise upon energization to detect the concentration of urea in the aqueous urea solution LQ1 and detect whether the liquid accommodated in the urea solution tank 10 is the aqueous urea solution LQ1 or a different type of liquid having a different thermal conductivity therefrom. It should be noted that, as shown in FIG. 3B, the lower end portion 511 has a main surface 511A constituted by the aforementioned ceramic layer 519A as well as a reverse surface 511B which is parallel thereto and is constituted by the ceramic layer 519B. Meanwhile, the temperature rise detecting portion 510 has a temperature-rise-portion main surface 511AS included in the main surface 511A and a temperature-rise-portion reverse surface 511BS included in the reverse surface 511B.

Incidentally, one ceramic layer 519A of the aforementioned ceramic layer 519 is made thinner than the other ceramic layer 519B. For this reason, heat generated in the temperature rise detecting portion 510, specifically the internal heater wiring 518, is relatively easily transmitted to the ceramic layer 519A side as compared with the ceramic layer 519B, and the outside temperature is also made easily transmittable to the internal heater wiring 518 from the relatively thin ceramic layer 519A.

Each of the connection terminals 52 is formed by bending a metal plate of a predetermined shape into a U-shape. As for this connection terminal 52, its lower end portion 521 is formed into a shape extending toward the downward side, is connected by soldering to an unillustrated pad formed on the upper end portion 514 of the concentration sensor element 51, and is thus secured to the concentration sensor element 51. As a result, the connection terminal 52 (lower end portion 521) is connected to the internal lead wiring 517 through an unillustrated via conductor penetrating the one ceramic layer 519A. For this reason, upon application of a voltage across the pair of connection terminals 52, mainly the internal heater wiring 518 generates heat through the internal lead wirings 517. The resistance value of this internal heater wiring 518 varies according to its own temperature.

Meanwhile, a conductor 533 of a lead wire 532 of the connection cable 53 is electrically and mechanically connected by soldering to an upper end portion 522 of the connection terminal 52. As shown in FIG. 1, this connection cable 53 is inserted in the inner cylinder 42, extends toward the vertically upward side Y2, and is connected to the wiring board 22 (control circuit).

In addition, the holder member 55 in its entirety is formed of an insulating resin material and, as shown in FIG. 2, it is a hollow member having a holder bore 55H penetrating itself in the vertical direction (up-down direction in FIG. 2). This holder bore 55H consists of three-stage circular hole portions including an inner cylinder holding bore 55H1, a second-stage bore 55H2, and a third-stage bore 55H3 which respectively become gradually smaller in diameter from the upward side toward the downward side, as well as an element holding bore 55H4 in the shape of a substantially square hole which is located on the most distal end side (lower side in the drawing).

This holder member 55 holds the concentration sensor element 51. Specifically, the insertion portion 512 of the concentration sensor element 51 is inserted in the element holding bore 55H4 of this holder member 55, and the resin holding portion 513 of the concentration sensor element 51 disposed in the third-stage bore 55H3 is fixed by a sealing resin 59 filled in this third-stage bore 55H3. It should be noted that the gap between the concentration sensor element 51 and the holder member 55 is liquid-tightly sealed by this sealing resin 59. Consequently, the lower end portion 511 having the internal heater wiring 518 disposed therein in this concentration sensor element 51 is disposed in such a manner as to protrude toward the vertically downward side Y1 from the element holding bore 55H4 of the holder member 55.

In addition, as shown in FIG. 2, this holder member 55 holds the lower end portion 421 of the inner cylinder 42 within the inner cylinder holding bore 55H1 of its holder bore 55H, and the holder member 55 at its inner cylinder abutment surface 55D located between this inner cylinder holding bore 55H1 and the second-stage bore 55H2 abuts against a lower end 422 of the inner cylinder 42 to thereby position the inner cylinder 42 and the holder member 55 in the axial direction (vertical direction Y).

Two O-ring insertion grooves 55G1 and 55G2 are provided in the inner cylinder holding bore 55H1 of the holder insertion bore 55H, and O-rings 571 and 572 disposed therein liquid-tightly seal the holder member 55 and the inner cylinder 42 (insulating film 43) and hold the inner cylinder 42.

Since the inner cylinder 42 and the holder member 55 holding the concentration sensor element 51 are connected as described above, a major portion of the upper end portion 514 of the concentration sensor element 51 and the entire connection terminals 52 are disposed in the inner cylinder 42. A separator 54, which is formed of an insulating resin having rubber-like elasticity to elastically hold the concentration sensor element 51 and the connection terminals 52 within the inner cylinder 42, is disposed in the lower end portion 421 of this inner cylinder 42 while insulating the concentration sensor element 51 and the connection terminals 52 from the inner cylinder 42.

Next, a description will be given of the enclosing member 58 of the urea concentration sensor portion 5.

As shown in FIG. 2, the enclosing member 58 has a bottomed cylindrical shape (i.e., a cylinder having a bottom wall) and includes a cylindrical side wall 581 and a bottom wall 582 which closes the lower end of the side wall 581. Three circular vents 58H1, 58H2, and 58H3, as well as a keyhole-like vent 58H4 consisting of a circular hole portion 58H41 (FIG. 4) and an elongated slit portion 58H42 extending therefrom toward the leading end side, are formed in the side wall 581 in such a manner as to be arranged at equal intervals in the circumferential direction so as to render the aqueous urea solution LQ1 circulatable in and outside this enclosing member 58. It should be noted that the vents 58H1, 58H2, and 58H3 and the circular hole portion 58H41 of the vent 58H4 are respectively formed as upper vents located closer to the vertically upward side than the lower end of the temperature rise detecting portion 510 of the concentration sensor element 51 when the urea sensor 1 is set in its attitude of being installed in the urea solution tank 10, as shown in FIG. 2 and FIGS. 4 to 7. In this embodiment, the diameter of each of the vents 58H1, 58H2, and 58H3 and the circular hole portion 58H41 of the vent 58H4, which are the upper vents, is set to 3.0 mm. In other words, each of these upper vents has such a form as to allow an hypothetical circle with a diameter (maximum diameter) of 3.0 mm to be disposed therein.

In addition, one circular lower circulation hole 58H6 is similarly formed in the center of the bottom wall 582 so as to render the aqueous urea solution LQ1 circulatable in and outside this enclosing member 58. This lower vent 58H6 is provided with a form in which it faces the vertically downward side when the urea sensor 1 is set in its attitude of being installed in the urea solution tank 10, as shown in FIG. 2.

It should be noted that, in this embodiment, the diameter of the lower vent 58H6 is set to 5.0 mm. Namely, as shown by the two-dot chain lines of hatching in FIG. 8, the lower vent 58H6 has such a form as to allow a hypothetical circle K with a diameter (maximum diameter) of not less than 3.5 mm (5.0 mm in this embodiment) to be disposed therein. In addition, as can be appreciated from these descriptions, in this embodiment, the diameter (maximum diameter) of the hypothetical circle K included in the lower vent 58H6 is set to be greater than the diameter (maximum diameter) of the hypothetical circle included in each of the upper vents 58H1, 58H2, and 58H3 and the circular hole portion 58H41 of the vent 58H4, i.e., the upper vents, and is set to a size less than or equal to two-fold the maximum diameter of the hypothetical circle included in each of these upper vents.

Figure 9:
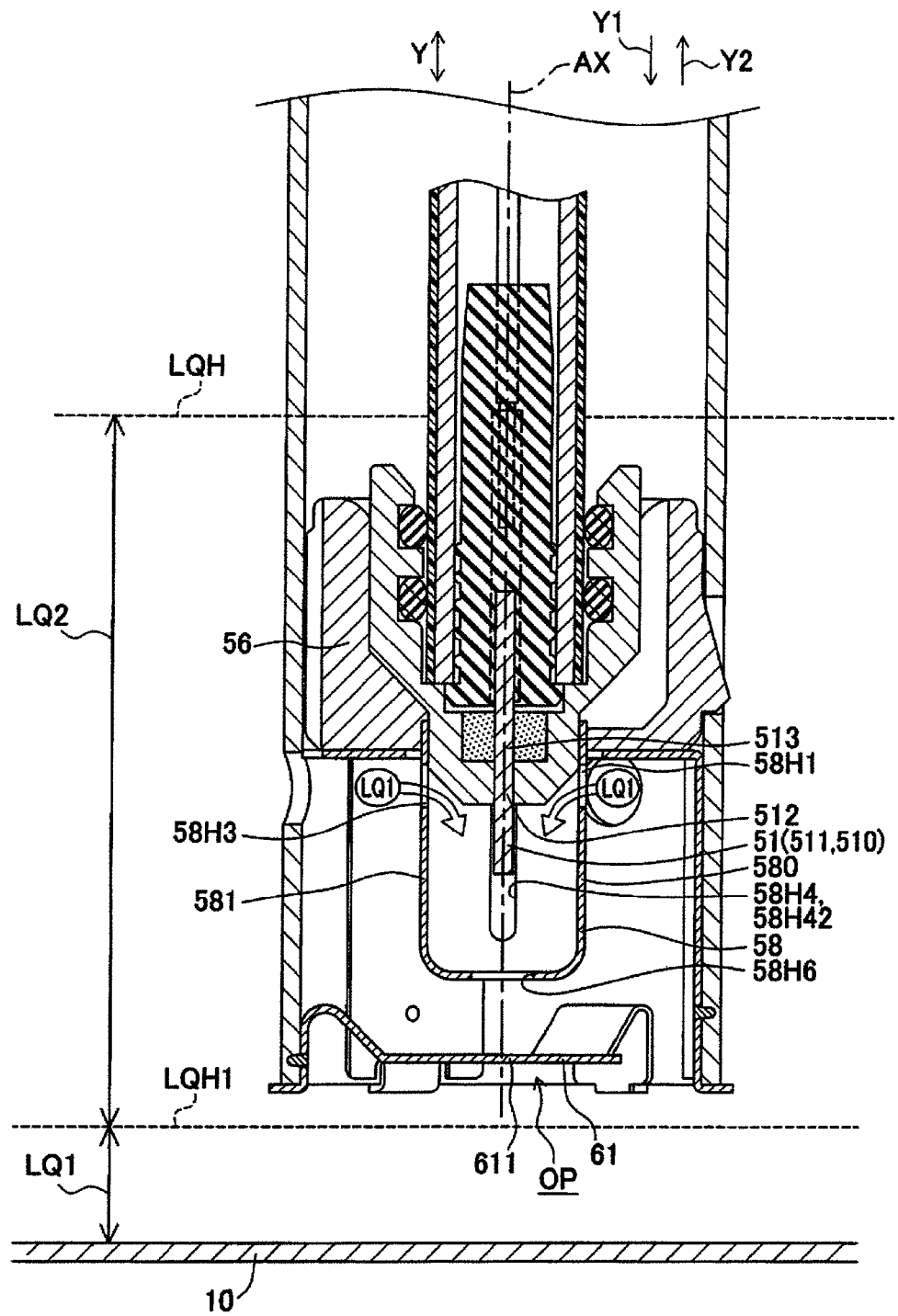
FIG. 9 is a side sectional view of a portion of the exemplary urea sensor of FIG. 1 immersed in a urea solution tank at a time when an aqueous urea solution LQ1 and light oil LQ2 are accommodated in the urea solution tank.

There is a possibility that a driver of a diesel powered automobile or an operator mistakenly adds light oil LQ2 (liquid of a different type) into the urea solution tank 10 by mistaking the urea solution tank 10 for a light oil tank, as shown in FIG. 9. It should be noted that since the light oil LQ2 has a smaller specific gravity than the aqueous urea solution LQ1, in the event that the light oil LQ2 has been added to the urea solution tank 10, the aqueous urea solution LQ1 comes to be located on the vertically downward side, while the light oil LQ2 comes to be located on the vertically upward side. In this case, in the state in which the aqueous urea solution LQ1 has decreased due to use and the liquid level LQH has dropped below the lower end of the temperature rise detecting portion 510, if the liquids (aqueous urea solution LQ1 and light oil LQ2) in the urea solution tank 10 violently move due to the effect of vibration and the like, there have been cases where droplets of the aqueous urea solution LQ1 enter the interior of the enclosing member 58 through the vents 58H1 to 58H4 and the like, as shown by arrows in FIG. 9.

However, according to an investigation made by the present inventors, there have been cases where even if vents are provided in a lower portion of the enclosing member for the purpose of liquid circulation, the aqueous urea solution which entered the interior of the enclosing member cannot be appropriately discharged to outside the enclosing member, and the aqueous urea solution accumulates only inside the enclosing member even if the light oil is located outside (around the periphery of) the enclosing member, thereby setting the detecting portion (temperature rise detecting portion) in a state of being surrounded by the aqueous urea solution. In that case, despite the abnormal situation in which the liquid level of the aqueous urea solution has dropped below the detecting portion (temperature rise detecting portion) and the light oil which has been erroneously poured into the urea solution tank might be supplied to the catalyst, there has been a possibility that the urea sensor erroneously detects that the appropriate aqueous urea solution is being accommodated in the urea solution tank.

Liquid Passage Test 1

Accordingly, the diameter of the lower vent 58H6 provided in the lower end portion (bottom portion) of the enclosing member 58 was varied, and an examination was made as to whether or not droplets of the aqueous urea solution LQ1 which entered the interior of the enclosing member 58 in the above-described manner were appropriately discharged to the outside. Specifically, four kinds of samples (which are set as Samples 1, 2, 3, and 4 in order) were prepared in which the holder 55, the concentration sensor element 51, and the like were fitted to the respective enclosing members of four kinds which differed only in that the diameter of the lower vent 58H6 was varied to 3.0 mm, 3.5 mm, 4.0 mm, and 5.0 mm. It should be noted that the diameter of each of the upper vents 58H1, 58H2, and 58H3 and the circular hole portion 58H41 of the vent 58H4, i.e., the upper vents, was set to 3.0 mm.

Next, these samples were immersed in the light oil which was placed in the tank and was in a stationary state, and the aqueous urea solution was slowly poured into the enclosing member 58 through the vents 58H1 to 58H4 of the enclosing member 58. Then, in Samples 1, 2, and 3 in which the diameter of the lower vent 58H6 was respectively set to 3.0 mm, 3.5 mm, and 4.0 mm, the aqueous urea solution gradually accumulated in the enclosing member 58, and the aqueous urea solution unfavorably accumulated up to the periphery of the temperature rise detecting portion 510. On the other hand, in Sample 4 in which the diameter of the lower vent 58H6 was set to 5.0 mm, the aqueous urea solution smoothly passed through the lower vent 58H6, and the aqueous urea solution did not accumulate up to the periphery of the temperature rise detecting portion 510.

Liquid Passage Test 2

Next, under the condition in which vibrations (20 Hz vibrations in this test) which were assumed to be vibrations at the time of the idling of the vehicle were applied to the tank with the light oil accommodated therein, the four kinds of samples prepared in the above-described Liquid Passage Test 1 were immersed in the light oil in the tank, and the aqueous urea solution was slowly poured into the tank. Then, in Sample 1 in which the diameter of the lower vent 58H6 was set to 3.0 mm, the aqueous urea solution gradually accumulated in the enclosing member 58, and the aqueous urea solution unfavorably accumulated up to the periphery of the temperature rise detecting portion 510. On the other hand, in Samples 2, 3, and 4 in which the diameter of the lower vent 58H6 was respectively set to 3.5 mm, 4.0 mm, and 5.0 mm, the aqueous urea solution smoothly passed through the lower vent 58H6, and the aqueous urea solution did not accumulate up to the periphery of the temperature rise detecting portion 510.

From these results, it can be said that, by setting the diameter of the lower vent to not less than 5.0 mm, in the case where the tank is in a stationary state, even if droplets of the aqueous urea solution enter the interior of the enclosing member, they can be discharged to outside the enclosing member through the lower vent, and therefore the light oil can be located around the temperature rise detecting portion 510 as around the outer portion (periphery) of the enclosing member. In addition, it can be said that, by setting the diameter of the lower vent to not less than 3.5 mm, if vibrations of such a level as applied frequently to the urea solution tank are exerted, even if droplets of the aqueous urea solution enter the interior of the enclosing member, they can be discharged to outside the enclosing member through the lower vent, and therefore the light oil can be located around the temperature rise detecting portion 510 as around the outer portion (periphery) of the enclosing member.

In the urea sensor 1 in accordance with this embodiment, the lower vent 58H6 with a diameter of 5.0 mm is provided in the enclosing member 58, as described above. Accordingly, in the urea sensor 1 in accordance with this embodiment, it is possible to prevent the defect of erroneously detecting that the appropriate aqueous urea solution is being accommodated in the urea solution tank 10 in the case where the light oil LQ2 is erroneously accommodated in the urea solution tank 10 and the liquid level LQH of the aqueous urea solution LQ1 has dropped below the temperature rise detecting portion 510 (see FIG. 9) Namely, it is possible to appropriately detect that a different type of liquid (light oil LQ2) is present in the urea solution tank 10.

Figure 12:
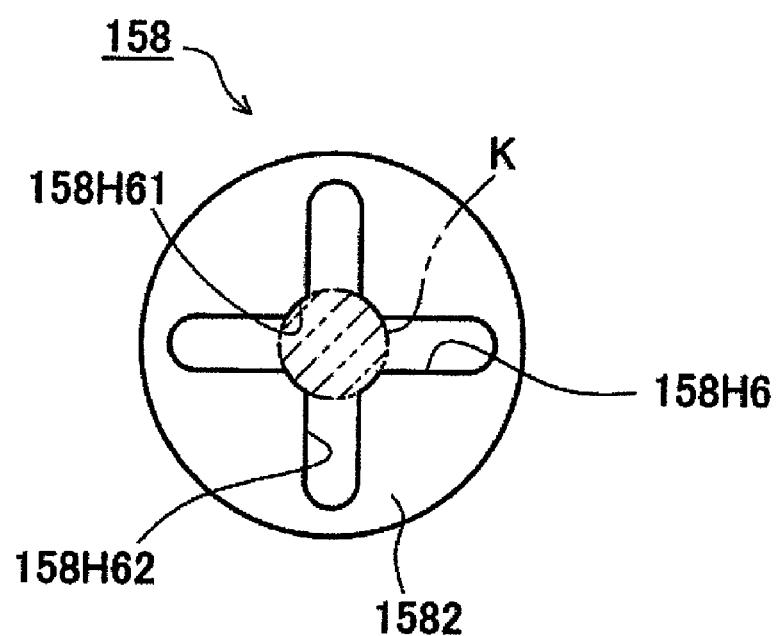
FIG. 12 is a bottom plan view of an exemplary enclosing member showing a lower vent of another form.
Figure 13:
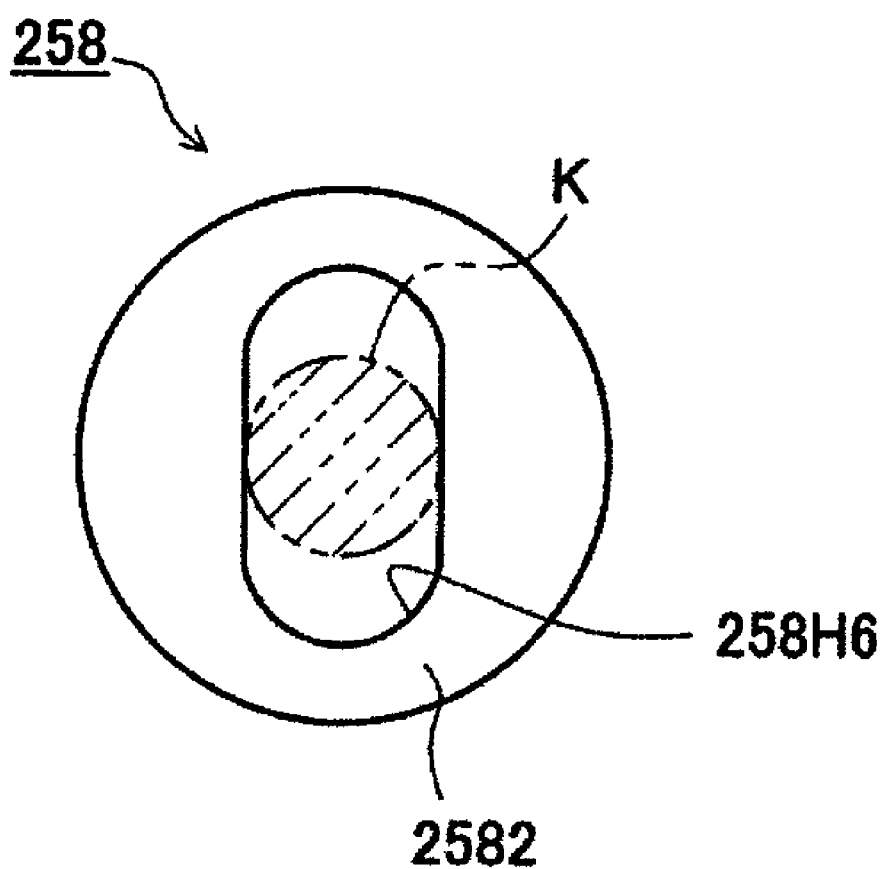
FIG. 13 is a bottom plan view of an exemplary enclosing member showing a lower vent of still another form.

It should be noted that although in these liquid passage tests the shape of the lower vent is set to be circular, the form of the lower vent is not limited to the circular shape and may be any form. Accordingly, from the results of these tests, conceivably, it suffices if the form is set such that the lower vent can be disposed inside the hypothetical circle K with a diameter of not less than 3.5 mm (preferably not less than 5.0 mm). For example, as in an enclosing member 158 shown in FIG. 12, the lower vent may be a lower vent 158H6 consisting of a circular vent 158H61 (in which the hypothetical circle K can be disposed) with a diameter of not less than 3.5 mm and four slits 158H62 extending radially from this vent 158H61. In addition, as shown in an enclosing member 258 in FIG. 13, the lower vent may be a lower vent 258H6 of an elliptical shape with a short diameter (dimension in the left-right direction in FIG. 13) of not less than 3.5 mm.

Furthermore, although in these liquid passage tests the lower vent was provided in the lower end portion (bottom portion) of the enclosing member, the position of the lower vent is not limited to the bottom wall of the enclosing member. Namely, it suffices if the position of the lower vent is such that droplets of the aqueous urea solution which entered the interior of the enclosing member can be discharged to the outside so as not to accumulate up to the periphery of the temperature rise detecting portion 510. Accordingly, the lower vent is conceivably sufficient if at least a portion of the lower vent is located closer to the vertically downward side than the temperature rise detecting portion 510 when the urea sensor is set in its attitude of being installed in the urea solution tank 10.

Figure 10:
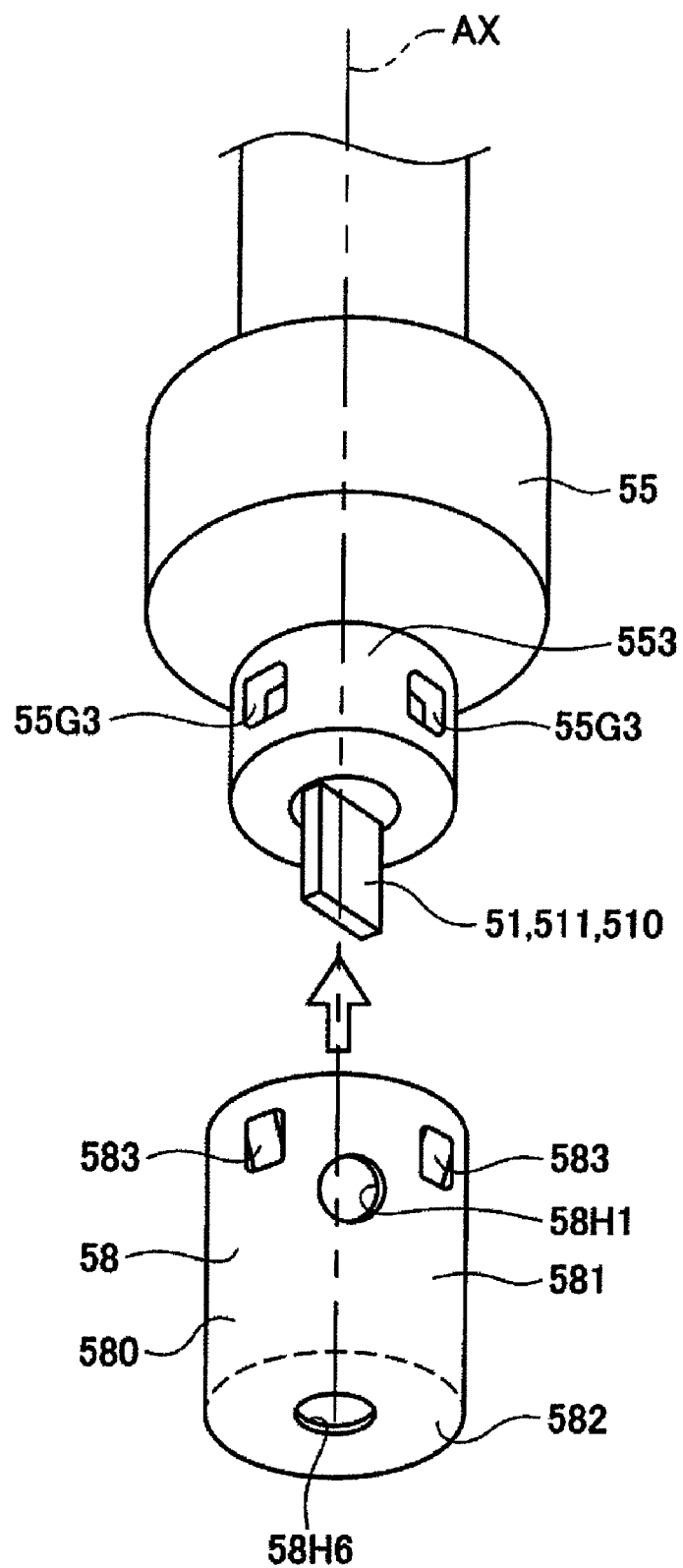
FIG. 10 is a partial perspective view showing a manner of connection between a holder member and the enclosing member of the urea sensor of FIG. 1.

In addition, four retaining tongue portions 583, which are provided by forming U-shaped cut-ins and bending them inward, are formed in vicinities of the upper end of the side wall 581 of the enclosing member 58 in such a manner as to be arranged at equal intervals in the circumferential direction. As a result, as shown in FIG. 10, enclosing member retaining recesses 55G3 formed in an outer periphery of the small-diameter portion 553 of the holder member 55 can be respectively retained by the retaining tongue portions 583 of the enclosing member 58. Consequently, an enclosing portion 580 of this enclosing member 58 is disposed so as to enclose the temperature rise detecting portion 510 of the concentration sensor element 51.

As shown in FIGS. 4 to 7, the vents 58H1, 58H2, 58H3, and 58H41 are formed at equal intervals in the circumferential direction in the side portion 581 of the enclosing member 58 surrounding the periphery of the temperature rise detecting portion 510. Further, as shown in FIG. 8, the lower vent 58H6 is formed in the bottom wall 587 of the enclosing member 58. For this reason, in the case where a liquid flow has occurred in the urea solution tank 10, the liquid flow can possibly enter the interior of the enclosing member 58 through any of the vents 58H1 to 58H4 and the lower vent 58H6 without weakening of the momentum of the liquid flow.

At this time, in a case where any one of the vents 58H1 to 58H4 and the lower vent 58H6 is disposed at a position frontally or directly facing the temperature-rise-portion main surface 511AS or the temperature-rise-portion reverse surface 511BS of the concentration sensor element 51, the liquid adjacent to the temperature-rise-portion main surface 511AS or the temperature-rise-portion reverse surface 511BS can move violently. This can possibly make it impossible for the temperature rise detecting portion 510 to appropriately perform the detection of whether the liquid accommodated in the urea solution tank 10 is the aqueous urea solution LQ1 or a different type of liquid (such as light oil) having a different thermal conductivity therefrom as well as the detection of the urea concentration.

Figure 7:
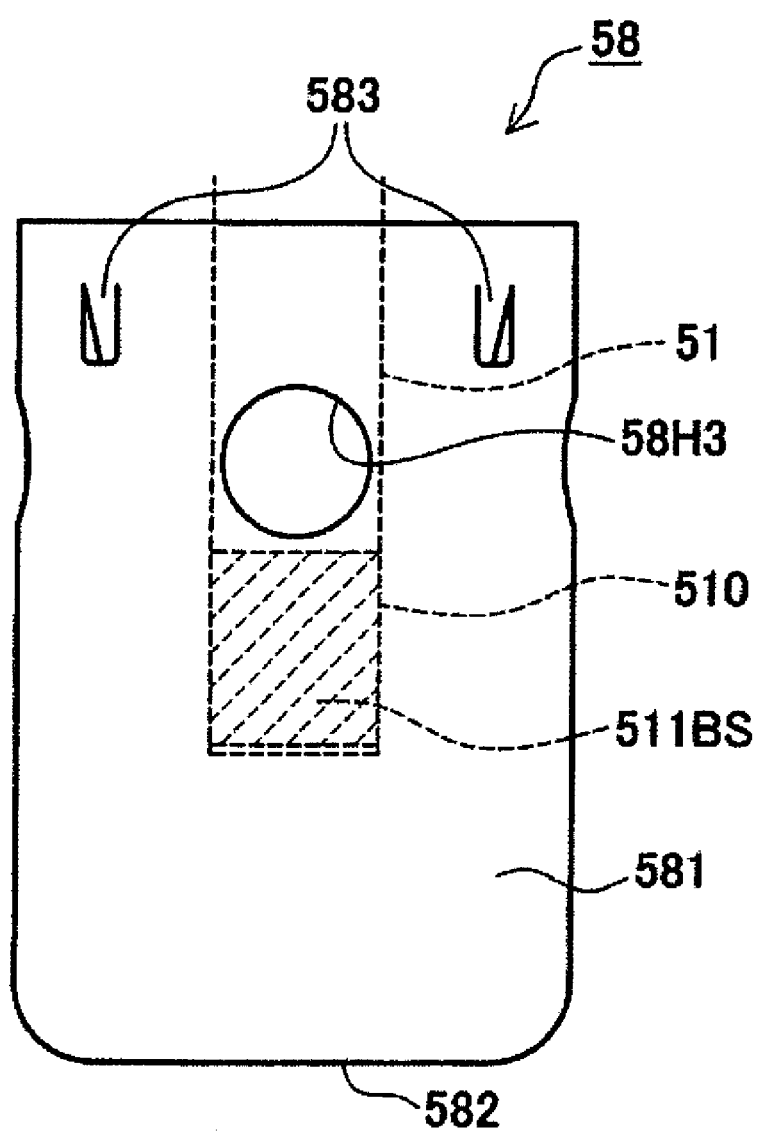
FIG. 7 is a right side elevational view of the enclosing member of FIG. 4.
Figure 8:
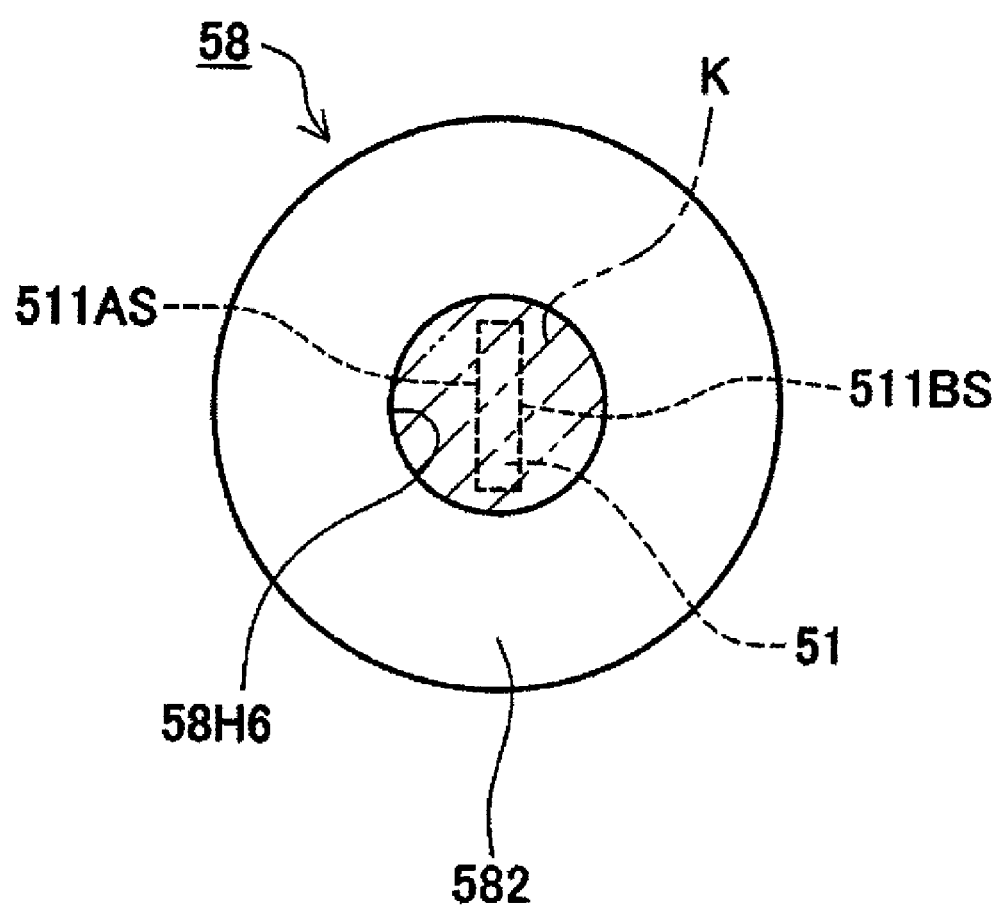
FIG. 8 is a bottom plan view of the enclosing member of FIG. 4.

By contrast, in the urea sensor 1 in accordance with this embodiment, as shown in FIGS. 4 to 8, as for the enclosing member 58, the respective vents 58H1 to 58H4 and the lower vent 58H6 are arranged at positions where they frontally face neither the temperature-rise-portion main surface 511AS (portion indicated by the broken lines of hatching in FIG. 5) nor the temperature-rise-portion reverse surface 511BS (portion indicated by the broken lines of hatching in FIG. 7). For this reason, even if the liquid flow enters the interior of the enclosing member 58 through the vents 58H1 to 58H4 and the lower vent 58H6, this liquid flow does not directly strike the temperature-rise-portion main surface 511AS and the temperature-rise-portion reverse surface 511BS, making it possible to prevent the violent movement of the liquid adjacent to the temperature-rise-portion main surface 511AS and the temperature-rise-portion reverse surface 511BS.

Therefore, in the urea sensor 1 in accordance with this embodiment, even if a liquid flow has occurred inside the urea solution tank 10, it is possible for the temperature rise detecting portion 510 to appropriately perform the detection of whether the liquid accommodated in the urea solution tank 10 is the aqueous urea solution LQ1 or a different type of liquid (such as light oil) having a different thermal conductivity therefrom as well as the detection of the urea concentration. It should be noted that, in FIGS. 4 to 8, the concentration sensor element 51 is indicated by the broken lines by way of reference so as to identify the position of the temperature rise detecting portion 510 in the urea sensor 1 with the enclosing member 58 fitted therein.

Further, the holder member 55 holding the concentration sensor element 51 and the enclosing member 58 is held by the insulating rubber bushing 56 having a holder holding hole 56H of a form which fits its outer peripheral surface. As shown in FIG. 2, this rubber bushing 56 has a hollow cylindrical bushing body portion 561 which has the aforementioned holder holding hole 56H formed in its center and has an outside diameter allowing fitting to the outer cylinder 41, as well as the retaining projecting portions 562 which are uniformly arranged at three positions on the outer periphery of this bushing body portion 561 and project radially outward from the bushing body portion 561. The holder holding hole 56H of the bushing body portion 561 is provided with such a shape as to be brought into close contact with the holder member 55 and the enclosing member 58 and to be capable of holding them.

This rubber bushing 56 is held by the outer cylinder 41 as the retaining projecting portions 562 are inserted in and retained at the holding holes 41H in the outer cylinder 41. As such, the holder member 55 holding both the concentration sensor element 51 and the enclosing member 58 is held by the rubber bushing 56, and as this rubber bushing 56 is held by the outer cylinder 41, the entire liquid concentration sensor portion 5 is held between the holding portion 412 of the outer cylinder 41 and the lower end portion 421 of the inner cylinder 42.

Furthermore, in this bushing body portion 561, a multiplicity of outer peripheral slits 561G extending in the vertical direction (up-down direction in FIG. 2) are provided in the outer peripheral surface of this bushing body portion 561 between adjacent ones of the retaining projecting portions 562. As the rubber bushing 56 is fitted in the outer cylinder 41, these outer peripheral slits 561G form circulation passages between this bushing body portion 561 and the outer cylinder 41 so as to allow the circulation of the aqueous urea solution LQ1 and debubbling in the vertical direction Y, as shown in FIG. 2.

Figure 11:
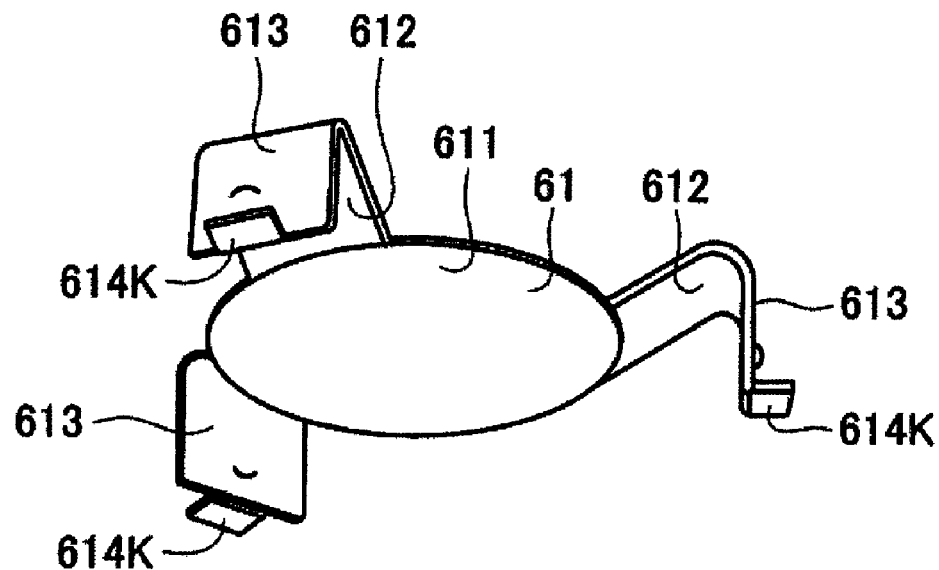
FIG. 11 is a perspective view of a flow controlling member of the urea sensor of FIG. 1.

Furthermore, a flow controlling member 61 is fitted in a leading end portion 411 of the outer cylinder 41. As shown in FIGS. 2 and 11, this flow controlling member 61 consists of a disk-shaped shielding portion 611 whose outside diameter is smaller than the inside diameter of the outer cylinder 41 and is greater than the outside diameter of the enclosing member 58, as well as three bridge portions 612 extending diagonally upward in FIG. 2 from a peripheral edge of this shielding portion 611 and reaching the leading end portion 411 of the outer cylinder 41. A plate-like portion 613, which has a curved plate shape and is inverted in the vertically downward direction Y1 so as to be disposed along an inner peripheral surface 41N of the leading end portion 411 of the outer cylinder 41, is further provided on each of the tips of these bridge portions 612. The leading end of this plate-like portion 613 is bent radially outwardly of the outer cylinder 41 and is thereby formed as an engaging pawl portion 614.

In the sensor 1 in accordance with this embodiment, as shown in FIG. 2, in a state in which the engaging pawl portions 416 at the tips of the plate-like portions 613 are engaged with the lower end 41T of the outer cylinder 41, the flow controlling member 61 is spot-welded at welds 613W of the plate-like portions 613 to the leading end portion 411 of the outer cylinder 41. As a result, a portion (central portion) of the lower end opening OP of the outer cylinder 41 is set in a state of being closed by the shielding portion 611 of the flow controlling member 61.

The shielding portion 611 of this flow controlling member 61 has a flow controlling surface 611B which is provided on the vertically downward side Y1 of the lower vent 58H6 formed in the lower end portion 582 of the enclosing member 58, and which opposes the hypothetical circle K of the lower vent 58H6. Further, as shown in FIG. 2, this flow controlling surface 611B is set in a form in which the lower vent 58H6 (hypothetical circle K) in its entirety is included in a projected region TR of the flow controlling surface 611B when the flow controlling surface 611B is projected onto the vertically upward side Y2 (toward the lower vent 58H6). In other words, when the urea sensor 1 is set in the attitude of being installed in the urea solution tank 10, and the vertically upward side Y2 is viewed from the vertically lower side (lower side in FIG. 2) of the urea sensor 1, the lower vent 58H6 is shielded by the shielding portion 611 of the flow controlling member 61 (by the portion constituting the flow controlling opposing surface 611B of the flow controlling member 61).

By so doing, even if a liquid flow directed from the vertically lower side toward the vertically upper side Y2 of the urea sensor 1 has occurred in the urea solution tank 10, it is possible to prevent this liquid flow from entering the enclosing member 58 directly through the lower vent 58H6 by virtue of the presence of the shielding portion 611 of the flow controlling member (portion constituting the flow controlling opposing surface 611B of the flow controlling member 61). As a result, it is possible to appropriately suppress the effect exerted by such a liquid flow on the detection of whether the liquid accommodated in the urea solution tank 10 is the aqueous urea solution LQ1 or a different type of liquid (such as light oil) having a different thermal conductivity therefrom as well as on the detection of the urea concentration. In other words, it is possible to prevent the aqueous urea solution around the temperature rise detecting portion 510 from moving violently due to the effect of such a liquid flow, thereby making it possible for the temperature rise detecting portion 510 to appropriately perform the detection of whether the liquid accommodated in the urea solution tank 10 is the aqueous urea solution LQ1 or a different type of liquid (such as light oil) having a different thermal conductivity therefrom as well as the detection of the urea concentration.

Incidentally, the closer a distance L between the shielding portion 611 (flow controlling opposing surface 611B) of the flow controlling member 61 and the lower vent 58H6 (hypothetical circle K), the more it is possible to prevent the liquid flow directed from the vertically lower side toward the vertically upper side Y2 of the urea sensor 1 from entering the enclosing member 58 directly through the lower vent 58H6, which arrangement is therefore preferable. However, if the distance L is made too close, there has been a possibility that when droplets of the aqueous urea solution LQ1 have entered the interior of the enclosing member 58 with the light oil LQ2 accommodated in the urea solution tank 10, the discharge of the droplets of the aqueous urea solution LQ1 to outside the enclosing member 58 through the lower vent 58H6 is unfavorably hampered by the shielding portion 611 (flow controlling opposing surface 611B).

Liquid Passage Test 3

Accordingly, the distance L between the shielding portion 611 (flow controlling opposing surface 611B) of the flow controlling member 61 and the lower vent 58H6 (hypothetical circle K) was varied, and an examination was made as to whether or not droplets of the aqueous urea solution LQ1 which entered the interior of the enclosing member 58 could be appropriately discharged to the outside, in the same way as in the above-described Liquid Passage Test 1. Specifically, the enclosing member 58 in which the diameter of the lower vent 58H6 was uniformly set to 5.0 mm was used as the enclosing member, and three kinds of urea sensors (which are set as Samples 5, 6, and 7 in order) were prepared in which the distance L was varied to three kinds including 2.0 mm, 3.0 mm, and 4.0 mm.

Next, these samples were immersed in stationary light oil, and the aqueous urea solution was slowly poured into the enclosing member 58 through the vents 58H1 to 58H4 of the enclosing member 58. Then, in Sample 5 in which the distance L was set to 2.0 mm, the aqueous urea solution gradually accumulated in the enclosing member 58, and the aqueous urea solution unfavorably accumulated up to the periphery of the temperature rise detecting portion 510. On the other hand, in Samples 6 and 7 in which the distance L was set to 3.0 mm and 4.0 mm, respectively, the aqueous urea solution smoothly passed through the lower vent 58H6, and the aqueous urea solution did not accumulate up to the periphery of the temperature rise detecting portion 510.

From these results, it can be said that by setting the distance L between the shielding portion 611 (flow controlling opposing surface 611B) of the flow controlling member 61 and the lower vent 58H6 (hypothetical circle K) to not less than 3.0 mm, the discharge of droplets of the aqueous urea solution LQ1, which entered the interior of the enclosing member 58 as described above, to outside the enclosing member 58 through the lower vent 58H6 is not hampered by the shielding portion 611 (flow controlling opposing surface 611B). Namely, it can also be said that by setting the distance L to not less than 3.0 mm, droplets of the aqueous urea solution LQ1, which entered the interior of the enclosing member 58 as described above, can be appropriately discharged to outside the enclosing member 58 through the lower vent 58H6.

Next, a description will be given of the operation of the urea concentration sensor portion 5 of the sensor 1 in the detection of the urea concentration of the aqueous urea solution LQ1.

In the urea sensor 1 in accordance with this embodiment, an electric current of a predetermined magnitude is allowed to flow across the concentration sensor element 51 of the urea concentration sensor portion 5 for a predetermined time duration (e.g., 700 ms) from the control circuit configured on the wiring board 22 to cause the internal heater wiring 518 to generate heat. Thereupon, a change in the detection voltage is detected by the control circuit to detect the concentration of the aqueous urea solution LQ1. Specifically, a detection voltage corresponding to the magnitude of the resistance value of the internal heater wiring 518 is generated in the internal heater wiring 518. Accordingly, a change in this detection voltage is detected by the control circuit to detect the concentration of the aqueous urea solution.

Specifically, a detection voltage immediately after the start of energization of the concentration sensor element 51 and a detection voltage after the lapse of a predetermined time from the energization start are measured. By using an amount of change in the detection voltage in the meantime, the concentration of the aqueous urea solution corresponding to this amount of change is obtained from the relationship obtained in advance between the amount of change and the concentration of the aqueous urea solution.

Incidentally, since the light oil LQ2 has a small thermal conductivity as compared to the aqueous urea solution LQ1, its amount of change in the detection voltage becomes large as compared to the aqueous urea solution LQ1 irrespective of the urea concentration. Accordingly, if amounts of change in the detection voltage are obtained in advance with respect to the aqueous urea solution LQ1 of various urea concentrations, and their maximum value is set as a threshold Q, and if the actual amount of change of the detection value has become greater than the threshold Q, it can be determined that the light oil LQ2 is being accommodated in the urea solution tank 10. On the other hand, if the actual amount of change of the detection value is less than or equal to the threshold Q, it can be determined that the aqueous urea solution LQ1 is being accommodated in the urea solution tank 10. Thus, it is possible to obtain the urea concentration in the above-described manner.

It should be noted that in this embodiment the detection of the concentration of the aqueous urea solution LQ1 is effected by using a CPU and the like in the control circuit, and a signal representative of the concentration information obtained from this control circuit is outputted to an external circuit (e.g., an ECU) through the external connection cable 24. In this external circuit, on the basis of the signal representative of the inputted concentration information a determination is made as to whether or not the concentration of the aqueous urea solution LQ1 is within a proper range, and if it is not within the proper concentration range, processing such as informing the driver to that effect is carried out, as required. In addition, if it is determined that the light oil LQ2 is accommodated in the urea solution tank 10, processing such as informing the driver to that effect and prompting the driver to replace it with the aqueous urea solution is carried out, as required.

Although the present invention has been described above in the context of the embodiment, the present invention is not limited to the above-described embodiment, and it goes without saying that the present invention may be implemented with various modifications, as required, without departing from the scope of the invention.

For example, in the above-described embodiment, the sensor of the type in which the liquid level sensor portion 4 and the urea concentration sensor portion 5 are combined has been illustrated by way of example as the urea sensor 1. However, the invention is also applicable to a type which does not have the function of a liquid level sensor and to a type which does not have the outer cylinder.

In addition, although in the above-described embodiment a description has been given of a technique of detecting the concentration of the aqueous urea solution in the urea concentration sensor portion 5, it is also possible to measure the liquid temperature of the aqueous urea solution from a resistance value immediately after the energization of the concentration sensor element 51 (internal heater wiring 518). Accordingly, the urea sensor in accordance with the invention can also be used as a liquid temperature sensor for measuring a liquid temperature, in addition to the concentration of the aqueous urea solution.

In addition, although in the above-described embodiment the sensor having the wiring board 22 with the control circuit mounted thereon has been illustrated by way of example as the urea sensor 1. However, the urea sensor 1 in accordance with the invention is sufficient if it is provided with the liquid concentration detecting element, the holder member for holding the same, the enclosing member, and the like, and the urea sensor in accordance with the invention also includes a urea sensor of a type which does not include the control circuit.

This application is based on Japanese Patent application JP 2007-11838, filed Jan. 22, 2007, and Japanese Patent application JP 2007-324895, filed Dec. 17, 2007, the entire contents of which are hereby incorporated by reference, the same as if fully set forth herein.

DESCRIPTION OF REFERENCE NUMERALS AND SIGNS

1: urea sensor
10: urea solution tank
51: concentration sensor element
58: enclosing member
58H1, 58H2, 58H3, 58H5: vents
58H6: lower vent (vent)
61: flow controlling member
510: temperature rise detecting portion (detecting portion, temperature rise portion)
511: lower end portion
511AS: temperature-rise-portion main surface
511BS: temperature-rise-portion reverse surface
518: internal heater wiring (heating resistor)
519: ceramic layer (ceramic insulating substrate)
611B: flow controlling opposing surface
K: hypothetical circle (first hypothetical circle)
LQ1: urea aqueous solution
LQ2: light oil

What is claimed is:

1. A urea sensor comprising:
a detecting portion, which, in use, is immersed in a liquid accommodated in a urea solution tank, for detecting the thermal conductivity of the liquid so as to detect whether the liquid accommodated in the urea solution tank is an aqueous urea solution; and
an enclosing member enclosing a periphery of the detecting portion and including one or more vents penetrating the enclosing member;
wherein at least one of the one or more vents comprises a lower vent having a breadth of at least 3.5 mm, said lower vent being disposed such that at least a portion of the lower vent is located closer to a downwardly extending end of the urea sensor than the detecting portion when the urea sensor is positioned for installation in the urea solution tank.

2. The urea sensor according to claim 1, wherein the lower vent of the enclosing member faces the downwardly extending end of the urea sensor when the urea sensor is positioned for installation in the urea solution tank.

3. The urea sensor according to claim 2, further comprising:
a flow controlling member which has a flow controlling surface, the flow controlling member being disposed below and opposing the lower vent when the urea sensor is positioned for installation in the urea solution tank;
wherein the flow controlling surface has a configuration and size such that when the flow controlling surface is projected onto the enclosing member to produce a projected region on the enclosing member, the circle-lower vent is wholly contained within the projected region of the flow controlling surface; and
wherein the flow controlling surface and the lower vent are spaced apart by a distance not less than 3.0 mm.

4. The urea sensor according to claim 3, wherein the detecting portion comprises a temperature rise portion in which a heating resistor whose resistance value changes in correspondence with a temperature thereof is liquid-tightly sealed in a ceramic insulating substrate.

5. The urea sensor according to claim 4, wherein the temperature rise portion has a temperature-rise-portion main surface having a heat-generating area and a temperature-rise-portion reverse surface located opposite to the temperature-rise-portion main surface, and wherein the enclosing member has a cylindrical side wall including at least one upper vent, each of the at least one upper vent being disposed at a position which directly faces neither the temperature-rise-portion main surface nor the temperature-rise-portion reverse surface.

6. The urea sensor according to claim 1, wherein the enclosing member has a bottom wall and a cylindrical side wall extending upward from the bottom wall, wherein the lower vent is disposed in the bottom wall.

7. The urea sensor according to claim 1, wherein the detecting portion comprises a temperature rise portion in which a heating resistor whose resistance value changes in correspondence with a temperature thereof is liquid-tightly sealed in a ceramic insulating substrate.

8. The urea sensor according to claim 7, wherein the temperature rise portion has a temperature-rise-portion main surface having a heat-generating area and a temperature-rise-portion reverse surface located opposite to the temperature-rise-portion main surface, and wherein the enclosing member further includes at least one upper vent, the enclosing member being formed such that the at least one upper vent and the lower vent are disposed at positions which directly face neither the temperature-rise-portion main surface nor the temperature-rise-portion reverse surface.

9. A urea sensor comprising:
a detecting portion which, in use, is immersed in a liquid accommodated in a urea solution tank, for detecting the thermal conductivity of the liquid so as to detect whether the liquid accommodated in the urea solution tank is an aqueous urea solution; and
an enclosing member enclosing a periphery of the detecting portion and including a plurality of vents penetrating the enclosing member;
wherein the plurality of vents include a lower vent located closer to a vertically downwardly extending end of the urea sensor than the detecting portion when the urea sensor is positioned for installation in the urea solution tank, and an upper vent located closer to a vertically upwardly extending end of the urea sensor than a lower end of the detecting portion; and wherein a minimum breadth of the lower vent is greater than a minimum breadth of the upper vent.

10. The urea sensor according to claim 9, wherein the minimum breadth of the lower vent is not more than twice the minimum breadth of the upper vent.

11. The urea sensor according to claim 9, wherein the minimum breadth of the lower vent is not less than 3.5 mm.

12. The urea sensor according to claim 9, wherein the lower vent of the enclosing member faces the downwardly extending end of the urea sensor when the urea sensor is positioned for installation in the urea solution tank.

13. The urea sensor according to claim 12, further comprising:

a flow controlling member which has a flow controlling surface, the flow controlling member being disposed below and opposing the lower vent when the urea sensor is positioned for installation in the urea solution tank;

wherein the flow controlling surface is has a configuration and size such that when the flow controlling surface is projected onto the enclosing member to produce a projected region on the enclosing member, the lower vent is wholly contained within the projected region of the flow controlling surface; and wherein the flow controlling opposing surface and the lower vent are spaced apart by a distance not less than 3.0 mm.

14. The urea sensor according to claim 13, wherein the detecting portion comprises a temperature rise portion in which a heating resistor whose resistance value changes in correspondence with a temperature thereof is liquid-tightly sealed in a ceramic insulating substrate.

15. The urea sensor according to claim 14, wherein the temperature rise portion has a temperature-rise-portion main surface having a heat-generating area and a temperature-rise-portion reverse surface located on a side opposite to the temperature-rise-portion main surface, and wherein the one upper vent is disposed at a position which directly faces neither the temperature-rise-portion main surface nor the temperature-rise-portion reverse surface.

16. The urea sensor according to claim 9, wherein the enclosing member has a bottom wall and a cylindrical side wall extending upward from the bottom wall, wherein the lower vent is disposed in the bottom wall.

17. The urea sensor according to claim 9, wherein the detecting portion comprises a temperature rise portion in which a heating resistor whose resistance value changes in correspondence with a temperature thereof is liquid-tightly sealed in a ceramic insulating substrate.

18. The urea sensor according to claim 17, wherein the temperature rise portion has a temperature-rise-portion main surface having a largest heat-generating area and a temperature-rise-portion reverse surface located on a side opposite to the temperature-rise-portion main surface, and wherein the upper vent and the lower vent are disposed at positions which directly faces neither the temperature-rise-portion main surface nor the temperature-rise-portion reverse surface.

19. A urea sensor comprising:

a detecting portion, which, in use, is immersed in a liquid accommodated in a urea solution tank, for detecting the thermal conductivity of the liquid so as to detect whether the liquid accommodated in the urea solution tank is an aqueous urea solution; and an enclosing member enclosing a periphery of the detecting portion and including one or more vents penetrating the enclosing member;

wherein at least one of the one or more vents comprises a lower vent disposed such that at least a portion of the lower vent is located below the detecting portion when the urea sensor is positioned for installation in the urea solution tank, the lower vent being of a configuration and size such that the lower vent discharges aqueous urea solution from the enclosing member when a liquid having a smaller specific gravity is present in the urea solution tank.

\* \* \* \* \*

UNITED STATES PATENT AND TRADEMARK OFFICE
CERTIFICATE OF CORRECTION

PATENT NO. : 8,137,625 B2  
APPLICATION NO. : 12/016580  
DATED : March 20, 2012  
INVENTOR(S) : Sasanuma et al.

Page 1 of 1

It is certified that error appears in the above-identified patent and that said Letters Patent is hereby corrected as shown below:

IN THE CLAIMS:

In Claim 2, col. 22, line 18 delete the word "circle-" to change the text to read: "jected region on the enclosing member, the lower"

Signed and Sealed this  
Fifteenth Day of May, 2012

David J. Kappos  
*Director of the United States Patent and Trademark Office*